(12) United States Patent
Lee et al.

(10) Patent No.: US 11,758,808 B2
(45) Date of Patent: Sep. 12, 2023

(54) ORTHO-SUBSTITUTED THERMALLY ACTIVATED DELAYED FLUORESCENCE MATERIAL AND ORGANIC LIGHT-EMITTING DEVICE COMPRISING SAME

(71) Applicant: SAMSUNG DISPLAY CO., LTD., Yongin-si (KR)

(72) Inventors: Chilwon Lee, Yongin-si (KR); Myoungseon Gong, Seoul (KR); Jaeryung Cha, Cheonan-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 819 days.

(21) Appl. No.: 15/562,415

(22) PCT Filed: Nov. 25, 2015

(86) PCT No.: PCT/KR2015/012740
§ 371 (c)(1),
(2) Date: Jan. 15, 2018

(87) PCT Pub. No.: WO2016/159479
PCT Pub. Date: Oct. 6, 2016

(65) Prior Publication Data
US 2018/0123049 A1    May 3, 2018

(30) Foreign Application Priority Data
Mar. 27, 2015  (KR) .................. 10-2015-0043263

(51) Int. Cl.
*H01L 51/00*   (2006.01)
*C07D 403/10*  (2006.01)
(Continued)

(52) U.S. Cl.
CPC ......... *H10K 85/654* (2023.02); *C07D 209/82* (2013.01); *C07D 251/14* (2013.01);
(Continued)

(58) Field of Classification Search
None
See application file for complete search history.

(56) References Cited

U.S. PATENT DOCUMENTS 4,128,559 A    12/1978  Pond et al.
8,324,403 B2   12/2012  Yabe et al.
(Continued)

FOREIGN PATENT DOCUMENTS

CN    101087776 A    12/2007
JP    H11292860 A    10/1999
(Continued)

OTHER PUBLICATIONS

Machine English translation of Murata et al. (JP 11-292860). Aug. 14, 2020.*
(Continued)

*Primary Examiner* — Jay Yang
(74) *Attorney, Agent, or Firm* — Lewis Roca Rothgerber Christie LLP

(57) ABSTRACT

A thermally activated delayed fluorescent (TADF) material is provided. The TADF material has a form in which an electron donating group and an electron withdrawing group are connected to benzene and the electron withdrawing group is position in an ortho position to the electron donating group.

10 Claims, 1 Drawing Sheet

(51) Int. Cl.
    *C07D 251/24*     (2006.01)
    *C07D 491/048*     (2006.01)
    *C07D 403/14*     (2006.01)
    *C09K 11/06*     (2006.01)
    *H10K 85/60*     (2023.01)
    *C07D 209/82*     (2006.01)
    *C07D 251/14*     (2006.01)
    *H10K 50/00*     (2023.01)
    *H10K 50/11*     (2023.01)
    *H10K 50/15*     (2023.01)
    *H10K 50/16*     (2023.01)
    *H10K 101/30*     (2023.01)

(52) U.S. Cl.
    CPC ......... *C07D 251/24* (2013.01); *C07D 403/10* (2013.01); *C07D 403/14* (2013.01); *C07D 491/048* (2013.01); *C09K 11/06* (2013.01); *H10K 50/00* (2023.02); *H10K 85/636* (2023.02); *H10K 85/657* (2023.02); *H10K 85/6572* (2023.02); *C09K 2211/1018* (2013.01); *H10K 50/11* (2023.02); *H10K 50/15* (2023.02); *H10K 50/16* (2023.02); *H10K 2101/30* (2023.02)

(56) References Cited

U.S. PATENT DOCUMENTS

| | | | |
|---|---|---|---|
| 9,728,730 | B2 | 8/2017 | Kang et al. |
| 2008/0145699 | A1 | 6/2008 | Yabe et al. |
| 2013/0264560 | A1* | 10/2013 | Dobbs ................. C07D 401/14 257/40 |
| 2013/0306962 | A1* | 11/2013 | Yamamoto .......... H01L 51/5028 257/40 |
| 2016/0172599 | A1 | 6/2016 | Ogiwara et al. |
| 2016/0197286 | A1 | 7/2016 | Kawamura et al. |
| 2016/0211462 | A1 | 7/2016 | Ogiwara et al. |
| 2018/0019428 | A1 | 1/2018 | Kawamura |

FOREIGN PATENT DOCUMENTS

| | | |
|---|---|---|
| KR | 20110105285 A | 9/2011 |
| KR | 20120082938 A | 7/2012 |
| KR | 20140076521 A | 6/2014 |
| KR | 20150122005 A | 10/2015 |
| KR | 20170115498 A | 10/2017 |
| WO | 1998025912 A1 | 6/1998 |
| WO | 2006067976 A1 | 6/2006 |
| WO | 2014092083 A1 | 6/2014 |
| WO | 2014094963 A1 | 6/2014 |
| WO | 2014146752 A1 | 9/2014 |
| WO | 2015000548 A1 | 1/2015 |
| WO | 2015159706 A1 | 10/2015 |
| WO | 2015198987 A1 | 12/2015 |

OTHER PUBLICATIONS

"Database Registry", Chemical Abstracts Service, Columbus, Acc. No. 1309114-89-3, abstract, XP-002788649.

Matsumoto, Shoji, et al., Heterocycles, vol. 91, No. 4, 2015, pp. 795-814.

Tao, Ye, et al., Advanced Materials, Material Views, vol. 26, 2014, pp. 7931-7958.

Hiroki Uoyama et al., Highly efficient organic light-emitting diodes from delayed fluorescence, Nature, Dec. 13, 2012, pp. 234-238, vol. 492, Macmillan Publishers Limited.

* cited by examiner

ORTHO-SUBSTITUTED THERMALLY ACTIVATED DELAYED FLUORESCENCE MATERIAL AND ORGANIC LIGHT-EMITTING DEVICE COMPRISING SAME

TECHNICAL FIELD

Example embodiments of the present invention relate to compounds for an organic light emitting diode and more specifically to thermally activated delayed fluorescence materials as the compounds for the organic light emitting diode.

BACKGROUND ART

OLED (organic light emitting device) is a self-emitting device, and has advantages of fast response time, excellent brightness, driving voltage and response rate characteristics, and implementing multi-color, as well as wide viewing angle and excellent contrast.

General organic light emitting diode may include an anode, a cathode, and an organic layer interposed between the anode and the cathode. The organic layer may include a hole injection layer, a hole transport layer, a light emitting layer, an electron transport layer, and an electron injection layer and the like. When a voltage is applied between the anode and the cathode, holes injected from the anode are moved to the light emitting layer via the hole transport layer, and electrons injected from the cathode moves to the light emitting layer via the electron transport layer. Carriers, such as the holes and electrons, recombine in the light emitting layer to generate excitons, and the excitons transition to a ground state to emit light.

The excitons generated when the organic light emitting diode is driven are stochastically in a singlet state of 25% and a triplet state of 75%. In the case of a fluorescent light emitting material, only excitons in the singlet state which is 25% of total excitons participate in luminescence, and the internal quantum efficiency remains at maximum 25%. In order to improve these properties, iridium or platinum complexes facilitating emitting from the triplet excitons can be used, and thereby allowing excellent quantum efficiency characteristics. However, these materials are expensive, and their applications are limited due to the instability of the blue light emitting material.

In order to solve this problem, recently, a thermally activated delayed fluorescent organic material are being developed. The thermally activated delayed fluorescent organic material has an energy difference of 0.3 eV or less between the singlet state and the triplet state of excitons. In this case, the up-conversion from the triplet state into the singlet state is allowed by heat corresponding to room temperature or device driving temperature, and the theoretical quantum efficiency of nearly 100% can be achieved.

DISCLOSURE

Technical Problem

However, it is known that the actual quantum efficiency of currently developed thermally activated delayed fluorescent organic materials is very different from the theoretical quantum efficiency and still needs to be improved.

Technical Solution

It is an object of example embodiments of the present invention to provide a thermally activated delayed fluorescent material and an organic light emitting diode including the same, which can improve quantum efficiency as the transition from a triplet state to a single state can be more efficiently performed.

In some example embodiments, a thermally activated delayed fluorescent (TADF) material is provided. The TADF material has a form in which an electron donating group and an electron withdrawing group are connected to benzene and the electron withdrawing group is position in an ortho position to the electron donating group.

Advantageous Effects

According to example embodiments of the present invention, as the compound introduced with the electron donating group and the electron withdrawing group at the ortho positions of the benzene ring can have reduced energy difference between the singlet and triplet excited states, up-conversion of the triplet excited states to the singlet excited states through reverse intersystem crossing by heat at room temperature or device operating temperature can easily occurs, which may result in delayed fluorescence.

DESCRIPTION OF DRAWINGS

Example embodiments of the present invention will become more apparent by describing in detail example embodiments of the present invention with reference to the accompanying drawings, in which.

MODES OF THE INVENTION

Figure 1:
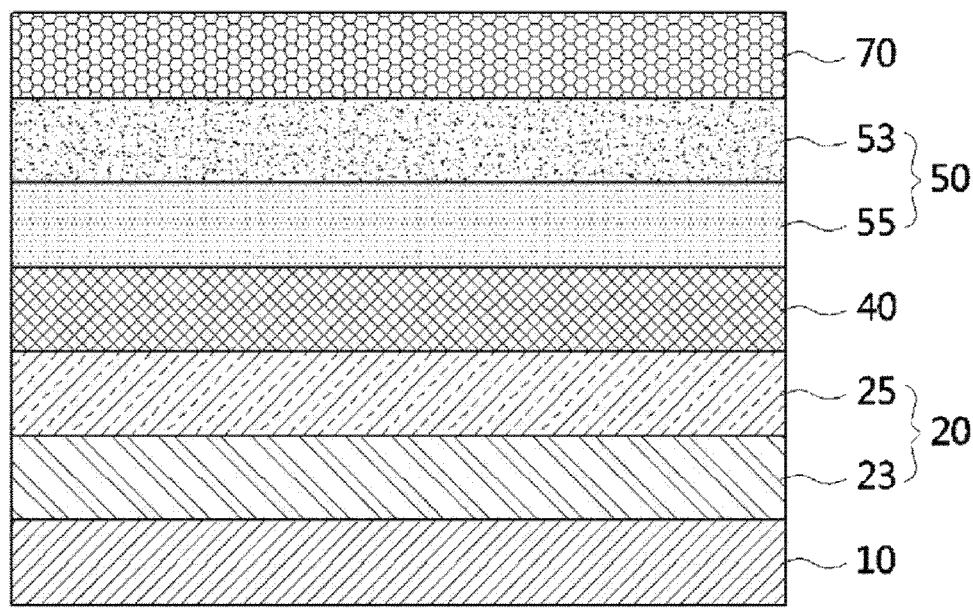
FIG. 1 is a cross-sectional view illustrating an organic light emitting diode according to an exemplary embodiment of the present invention.

Hereinafter, the present invention will be described in further detail with reference to several aspects and various exemplary embodiments. Hereinafter, exemplary embodiments of the present invention will be described in detail with reference to the accompanying drawings. The embodiments to be described below may be modified in several different forms, and the scope of the present invention is not limited to the embodiments. Rather, the embodiments are provided to further faithfully and fully explain this disclosure and to fully convey the scope of the present invention to those skilled in the art. Like reference numerals in the drawings denote like elements.

As used herein, the term "alkyl group" means an aliphatic hydrocarbon group, unless otherwise defined. The alkyl group may be a saturated alkyl group which does not contain any double or triple bonds. Or the alkyl group may be an unsaturated alkyl group comprising at least one double bond or triple bond. The alkyl group, whether saturated or unsaturated, may be branched, straight chain or cyclic. The alkyl group may be a C1 to C30 alkyl group. More specifically, the alkyl group may be a C1 to C10 alkyl group or a C1 to C6 alkyl group. For example, the C1 to C4 alkyl groups may be selected from the group consisting of methyl, ethyl, propyl, iso-propyl, n-butyl, iso-butyl, sec-butyl and t-butyl.

As used herein, the term "aryl group" means a monocyclic aromatic compound or a polycyclic aromatic compound composed of fused aromatic rings unless otherwise defined, and includes a heteroaryl group.

As used herein, "heteroaryl group", unless otherwise defined, is a monocyclic aromatic compound or a polycyclic aromatic compound composed of fused aromatic rings, which contains at least one heteroatom selected from the group consisting of N, O, S, Se, and P in at least one ring.

As used herein, the term "halogen group" means a group 7 element, for example, F, Cl, Br, or I, unless otherwise defined. As an example, the halogen group may be F.

When "Cx-Cy" is described in the present specification, the number of carbon atoms corresponding to all the integers between x and y is also to be interpreted as described.

Thermally Activated Delayed Fluorescent (TADF) Material

The following Chemical Formula 1 represents a compound according to one exemplary embodiment of the present invention.

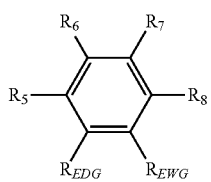

[Chemical Formula 1]

In the Chemical Formula 1, $R_{EDG}$ may be an electron donating group, $R_{EWG}$ may be an electron withdrawing group, $R_5$ to $R_8$ may be, independently of each other, a hydrogen atom, a heavy hydrogen atom, a substituted or unsubstituted C1-C9 alkyl group, a substituted or unsubstituted C5-C30 cycloalkyl group, a substituted or unsubstituted C6-C30 aryl group, a substituted or unsubstituted C6-C30 alkylaryl group, a substituted or unsubstituted C6-C30 aralkyl group, a substituted or unsubstituted C3-C30 heteroaryl group, a substituted or unsubstituted aryloxy group, a substituted or unsubstituted arylamine group, a substituted or unsubstituted fused arylamine group, a substituted or unsubstituted phosphine or phosphine oxide group, a substituted or unsubstituted thiol group, a substituted or unsubstituted sulfoxide or sulfone group.

The electron donating group may be a substituted or unsubstituted amine group, and the electron withdrawing group may be a substituted or unsubstituted triazine group.

The compound represented by Chemical Formula 1 may be a light emitting material. Specifically, it may be a thermally activated delayed fluorescent (TADF) material exhibiting thermally activated delayed fluorescence. More specifically, it can be used as a light emitting dopant in an organic light emitting device. However, it is not limited to this, and it may be used in any layer in the organic light emitting device, or may also be used as a host material in the light emitting layer.

The compound represented by Chemical Formula 1 has the form in which the electron donating group and the electron withdrawing group are bonded to benzene, and the electron withdrawing group is positioned in an adjacent position (ortho position) to the electron donating group. Thus, through the effect of steric hindrance by introducing the electron withdrawing group and the electron withdrawing group at ortho positions of benzene to each other, it is possible to control the overlapping of HOMO (Highest Occupied Molecular Orbital) and LUMO (Lowest Unoccupied Molecular Orbital) and reduce the difference between the singlet energy (S1) and the triplet energy (T1). Specifically, as the compound introduced with the electron withdrawing group and the electron withdrawing group at ortho positions of the benzene ring has a minimized energy difference between the singlet excited state and the triplet excited state (less than 0.3 eV), up-conversion of the triplet excited state to the singlet excited state through reverse intersystem crossing by heat at room temperature or device operating temperature can easily occurs, which may result in delayed fluorescence.

Specific examples of the compound represented by Chemical Formula 1 may be represented by any one of the following Chemical Formulas 2 to 4.

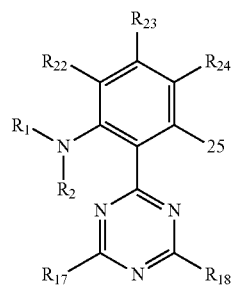

[Chemical Formula 2]

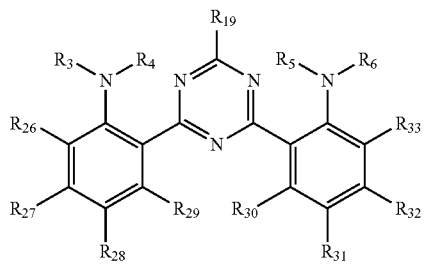

[Chemical Formula 3]

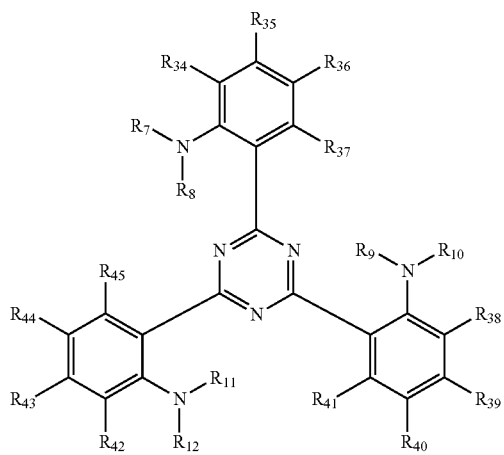

[Chemical Formula 4]

In Chemical Formulas 2 to 4, $R_1$ to $R_{12}$ may, independently of each other, represent a substituted or unsubstituted C1-C9 alkyl group, a substituted or unsubstituted C5-C30 cycloalkyl group, a substituted or unsubstituted C6-C30 aryl group, a substituted or unsubstituted C6-C30 alkylaryl group, a substituted or unsubstituted C6-C30 aralkyl group, or a substituted or unsubstituted C3-C30 heteroaryl group; $R_1$ and $R_2$, $R_3$ and $R_4$, $R_5$ and $R_6$, $R_7$ and $R_8$, $R_9$ and $R_{10}$, or $R_{11}$ and $R_{12}$ may be optionally combined together with the nitrogen to which they are attached to form a substituted or unsubstituted heterocyclyl or a substituted or unsubstituted heteroaryl group.

In Chemical Formulas 2 to 4, $R_{17}$ to $R_{19}$ may be functional groups connected to the triazine group through carbon, nitrogen, oxygen, silicon, sulfur, or phosphorus, and, independently of each other, a cyano group, a substituted or unsubstituted C1-C9 alkyl group, a substituted or unsubstituted C5-C30 cycloalkyl group, a substituted or unsubstituted C6-C30 aryl group, a substituted or unsubstituted C6-C30 alkylaryl group, a substituted or unsubstituted C6-C30 aralkyl group, a substituted or unsubstituted C3-C30 heteroaryl group, a substituted or unsubstituted C1-C30 alkyloxy group, a substituted or unsubstituted C3-C30 aryloxy group, a C1-C9 alkylsilyl group, or a substituted or unsubstituted $-NR_aR_b$. The $R_a$ and $R_b$ may be independently selected from the group consisting of hydrogen, heavy hydrogen, a substituted or unsubstituted C1-C9 alkyl group, a substituted or unsubstituted C5-C30 cycloalkyl group, a substituted or unsubstituted C6-C30 aryl group, a substituted or unsubstituted C6-C30 aralkyl group, or a substituted or unsubstituted C3-C30 heteroaryl group. The $R_a$ and $R_b$ may optionally be combined together with the nitrogen to which they are attached to form a substituted or unsubstituted heterocyclyl or a substituted or unsubstituted heteroaryl group.

Each of $R_{22}$ to $R_{45}$ may be the same as any one of $R_5$ to $R_8$ defined in the above Chemical Formula 1. Specifically, $R_{22}$ to $R_{45}$ may be, independently of each other, hydrogen, deuterium, a halogen group, a substituted or unsubstituted C4-C6 aryl group, or a substituted or unsubstituted C1-C3 alkyl group. Here, the substituted C1-C3 alkyl group may be a halogen-substituted C1-C3 alkyl group, and the halogen group may be F.

The electron donating group in Chemical Formula 1, or $-NR_1R_2$, $-NR_3R_4$, $-NR_5R_6$, $-NR_7R_8$, $-NR_9R_{10}$, or $-NR_{11}R_{12}$ in Chemical Formulas 2 to 4 may be, independently of each other, any one of Structural Formulas A1 to A19, for example, A6, A8, A9 or A10.

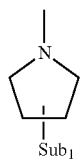
(A1)

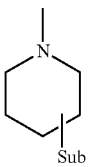
(A2)

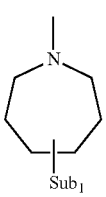
(A3)

(A4)

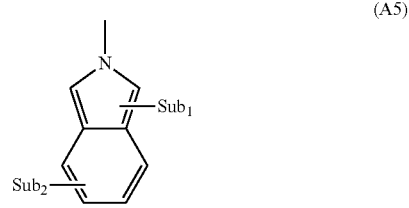
(A5)

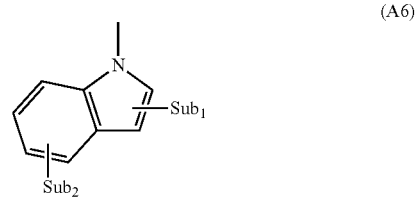
(A6)

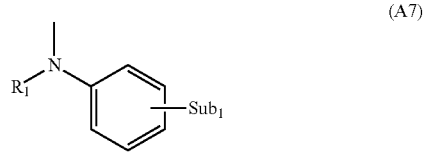
(A7)

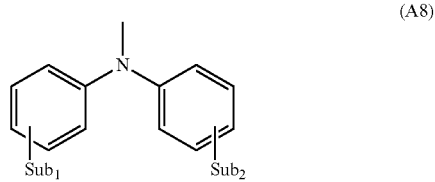
(A8)

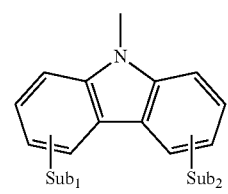
(A9)

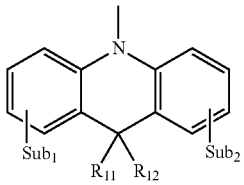
(A10)

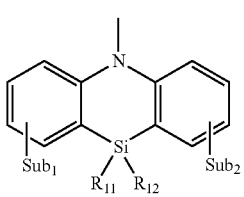
(A11)

In Structural Formulas A1 to A19,

R$_1$ is the same as R$_1$ in the above Chemical Formula 2,

R$_{11}$ to R$_{10}$ may be, independently of each other, hydrogen, deuterium, a substituted or unsubstituted C1-C2 alkyl group, or a substituted or unsubstituted C6-C30 aryl group, Sub$_1$ and Sub$_2$ may be, independently of each other, hydrogen, deuterium, a halogen group, a cyano group, a substituted or unsubstituted C1-C9 alkyl group, a substituted or unsubstituted C5-C30 cycloalkyl group, a substituted or unsubstituted C6-C30 aryl group, a substituted or unsubstituted C6-C30 alkylaryl group, a substituted or unsubstituted C3-C30 heteroaryl group, a substituted or unsubstituted C1-C9 alkyloxy group, a substituted or unsubstituted —NR$_c$R$_d$, a substituted or unsubstituted silyl group, a substituted or unsubstituted phosphine group, a substituted or unsubstituted phosphine oxide group, a substituted or unsubstituted thiol group, a substituted or unsubstituted sulfoxide group, a substituted or unsubstituted sulfone group, a substituted or unsubstituted C5-C30 arylsilyl group, a substituted or unsubstituted C5-C30 arylthio group, a substituted or unsubstituted C5-C30 aryloxy group, a substituted or unsubstituted C5-C30 arylamine group, or a substituted or unsubstituted C5-C30 aralkyl group. R$_c$ and R$_d$ may be, independently of each other, selected from the group consisting of a substituted or unsubstituted C1-C9 alkyl group, a substituted or unsubstituted C5-C30 cycloalkyl group, a substituted or unsubstituted C6-C30 aryl group, a substituted or unsubstituted C6-C30 aralkyl group, or a substituted or unsubstituted C3-C30 heteroaryl group. R$_c$ and R$_d$ may optionally be joined together with the nitrogen to which they are attached to form a substituted or unsubstituted heterocyclyl or a substituted or unsubstituted heteroaryl. Also, Sub$_1$ and Sub$_2$ may be, regardless of each other, optionally fused to a main body to which they are bonded to form a substituted or unsubstituted cyclic or a substituted or unsubstituted aryl. In particular, when at least one of Sub$_1$ and Sub$_2$ is a substituted or unsubstituted C5-C30 arylsilyl, a substituted or unsubstituted C5-C30 arylthio, a substituted or unsubstituted C5-C30 aryloxy, a substituted or unsubstituted C5-C30 arylamine group, or a substituted or unsubstituted C5-C30 aralkyl group, the aryl group contained therein may be fused to the main body to form a substituted or unsubstituted heterocyclyl or a substituted or unsubstituted heteroaryl.

The electron donating group in Chemical Formula 1, or —NR$_1$R$_2$, —NR$_3$R$_4$, —NR$_5$R$_6$, —NR$_7$R$_8$, —NR$_9$R$_{10}$, and —NR$_{11}$R$_{12}$ in Chemical Formulas 2 to 4 may be any of Structural Formulas A20 to A38, independently of each other. In particular, the Structural Formula A9 may be any one of the following Structural Formulas A20 to A38.

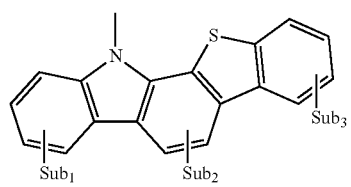
(A22)
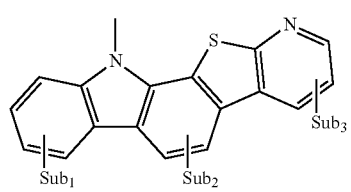
(A23)
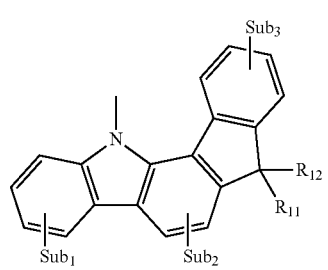
(A24)
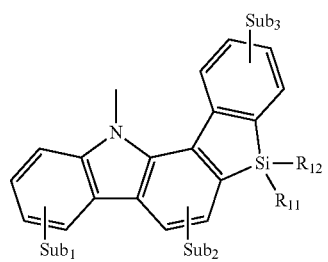
(A25)
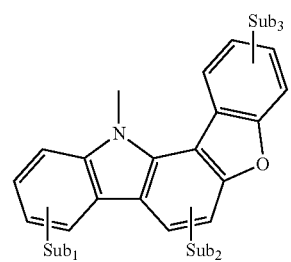
(A26)
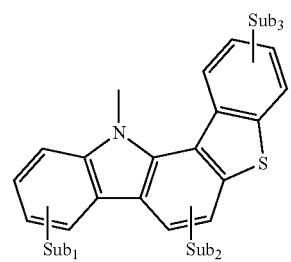
(A27)
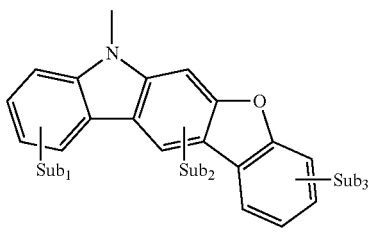
(A28)
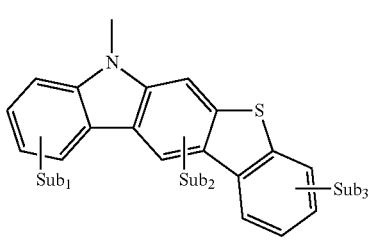
(A29)
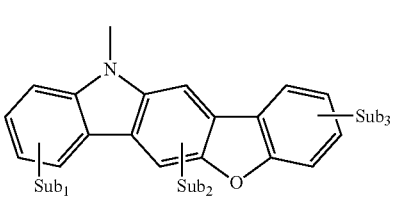
(A30)
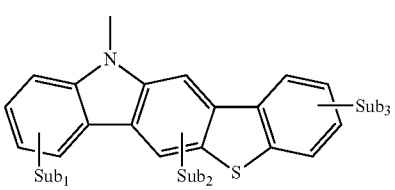
(A31)
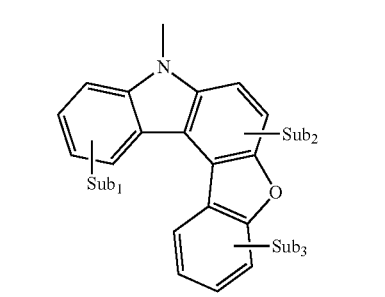
(A32)
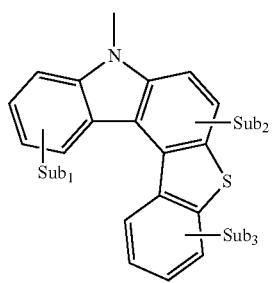
(A33)

-continued

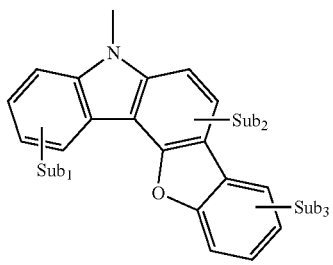
(A34)

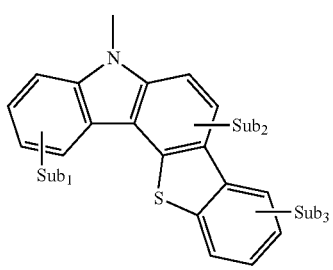
(A35)

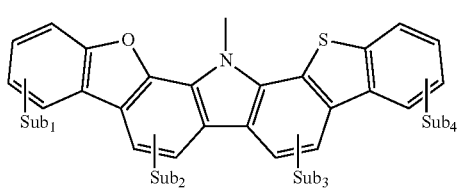
(A36)

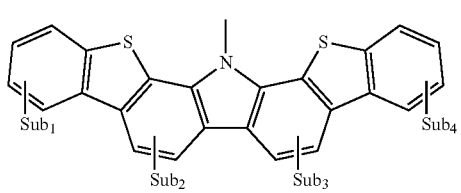
(A37)

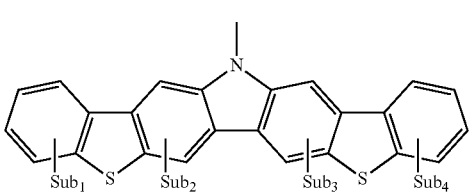
(A38)

In Structural Formulas A20 to A38, $R_{11}$ to $R_{10}$ may be, independently of each other, hydrogen, deuterium, a substituted or unsubstituted C1-C2 alkyl group, or a substituted or unsubstituted C6-C30 aryl group, $Sub_1$ to $Sub_4$ may be, independently of each other, hydrogen, deuterium, a halogen group, a cyano group, a substituted or unsubstituted C1-C9 alkyl group, a substituted or unsubstituted C5-C30 cycloalkyl group, a substituted or unsubstituted C6-C30 aryl group, a substituted or unsubstituted C6-C30 alkylaryl group, a substituted or unsubstituted C6-C30 aralkyl group, a substituted or unsubstituted C3-C30 heteroaryl group, a substituted or unsubstituted C1-C9 alkyloxy group, a substituted or unsubstituted C6-C30 aryloxy group, a substituted or unsubstituted silyl group, a substituted or unsubstituted phosphine group, a substituted or unsubstituted phosphine oxide group, a substituted or unsubstituted thiol group, a substituted or unsubstituted sulfoxide group, or a substituted or unsubstituted sulfone group.

The electron donating group in Chemical Formula 1, or —$NR_1R_2$, —$NR_3R_4$, —$NR_5R_6$, —$NR_7R_8$, —$NR_9R_{10}$, and —$NR_{11}R_{12}$ in Chemical Formulas 2 to 4 may be any of Structural Formulas A39 to A45, independently of each other. In particular, the Structural Formula A10 may be any one of the following Structural Formulas A39 to A45.

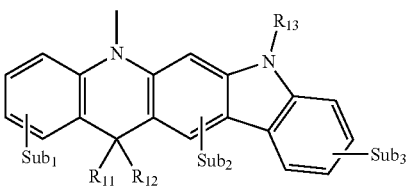
(A39)

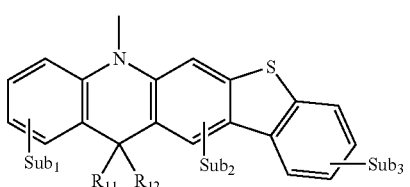
(A40)

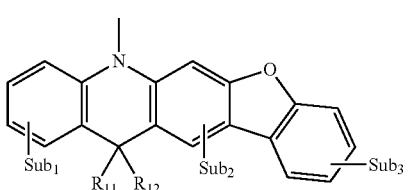
(A41)

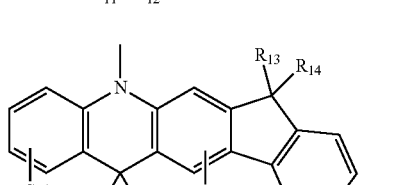
(A42)

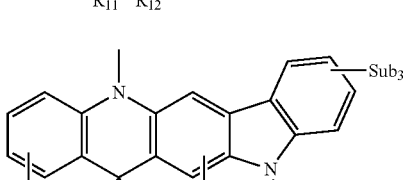
(A43)

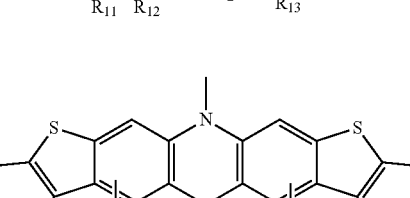
(A44)

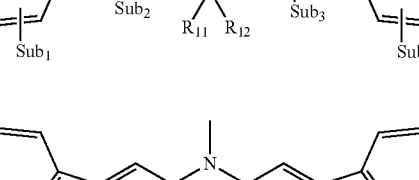
(A45)

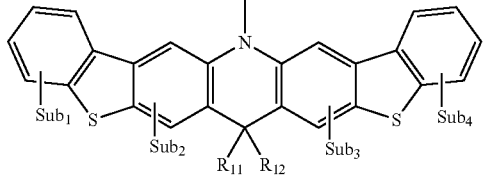

In Structural Formulas A39 to A45, $R_{11}$ to $R_{10}$ may be, independently of each other, hydrogen, deuterium, a substituted or unsubstituted C1-C2 alkyl group, or a substituted or unsubstituted C6-C30 aryl group, $Sub_1$ to $Sub_4$ may be, independently of each other, hydrogen, deuterium, a halogen group, a cyano group, a substituted or unsubstituted C1-C9 alkyl group, a substituted or unsubstituted C5-C30 cycloalkyl group, a substituted or unsubstituted C6-C30 aryl group, a substituted or unsubstituted C6-C30 alkylaryl group, a substituted or unsubstituted C6-C30 aralkyl group, a substituted or unsubstituted C3-C30 heteroaryl group, a substituted or unsubstituted C1-C9 alkyloxy group, a substituted or unsubstituted C6-C30 aryloxy group, a substituted or unsubstituted silyl group, a substituted or unsubstituted phosphine group, a substituted or unsubstituted phosphine oxide group, a substituted or unsubstituted thiol group, a substituted or unsubstituted sulfoxide group, or a substituted or unsubstituted sulfone group.

Examples of the electron withdrawing group in Chemical Formula 1 or the triazine group in Chemical Formula 2 may be the same as the following Structural Formulas B1 to B14.

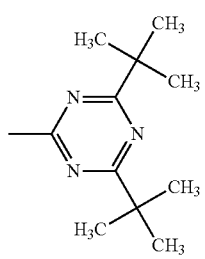
(B1)

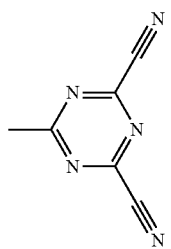
(B2)

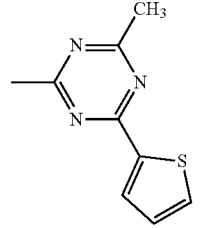
(B3)

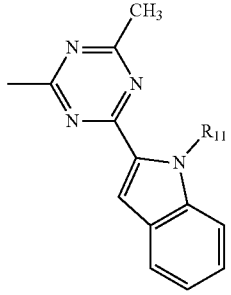
(B4)

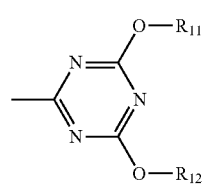
(B5)

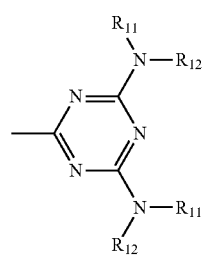
(B6)

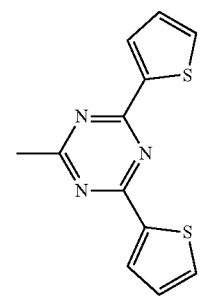
(B7)

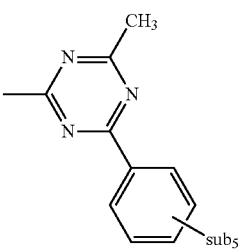
(B8)

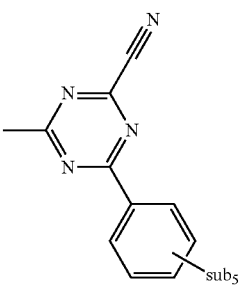
(B9)

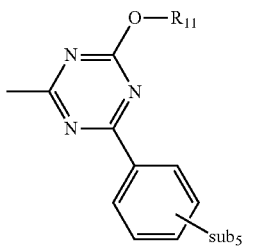
(B10)

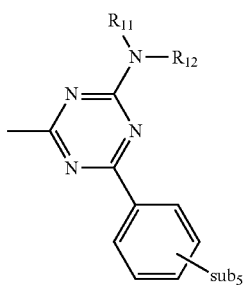
(B11)

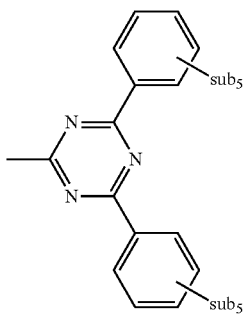
(B12)

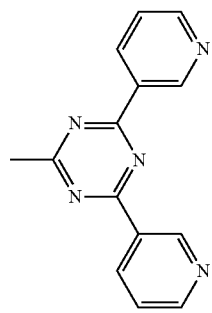
(B13)

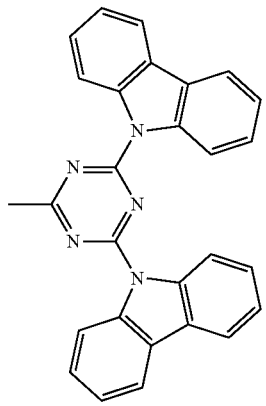
(B14)

In Structural Formulas B1 to B14, $R_{11}$ and $R_{12}$ may be, independently of each other, hydrogen, deuterium, or a substituted or unsubstituted C1-C2 alkyl group, $Sub_5$ and $Sub_6$ may be, independently of each other, hydrogen, deuterium, a halogen group, a cyano group, a substituted or unsubstituted C1-C9 alkyl group, a substituted or unsubstituted C6-C30 aryl group, a substituted or unsubstituted C3-C30 heteroaryl group, a substituted or unsubstituted C1-C9 alkyloxy group, a substituted or unsubstituted —$NR_eR_f$, a substituted or unsubstituted silyl group, a substituted or unsubstituted phosphine group, a substituted or unsubstituted phosphine oxide group, a substituted or unsubstituted thiol group, a substituted or unsubstituted sulfoxide group, a substituted or unsubstituted sulfone group, a substituted or unsubstituted C5-C30 arylthio group, a substituted or unsubstituted C5-C30 aryloxy group, a substituted or unsubstituted C5-C30 arylamine group, or a substituted or unsubstituted C5-C30 aralkyl group. Also, $Sub_5$ and $Sub_6$ may be, regardless of each other, optionally fused to a main body to which they are bonded to form a substituted or unsubstituted cyclic or a substituted or unsubstituted aryl. In particular, when $Sub_5$ or $Sub_6$ is a substituted or unsubstituted C5-C30 arylthio, a substituted or unsubstituted C5-C30 aryloxy, a substituted or unsubstituted C5-C30 arylamine group, or a substituted or unsubstituted C5-C30 aralkyl group, the aryl group contained therein may be fused to the main body to form a substituted or unsubstituted heterocyclyl or a substituted or unsubstituted heteroaryl.

$R_e$ and $R_f$ may be independently selected from the group consisting of a substituted or unsubstituted C1-C9 alkyl group, a substituted or unsubstituted C5-C30 cycloalkyl group, a substituted or unsubstituted C6-C30 aryl group, a substituted or unsubstituted C6-C30 alkylaryl group, a substituted or unsubstituted C6-C30 aralkyl group, or a substituted or unsubstituted C3-C30 heteroaryl group. $R_e$ and $R_f$ may optionally be joined together with the nitrogen to which they are attached to form a substituted or unsubstituted heterocyclyl or a substituted or unsubstituted heteroaryl.

Examples of the electron withdrawing group in the above Chemical Formula 1 or the triazine group substituted with $R_{17}$ and $R_{18}$ in the above Chemical Formula 2 may be the same as the following Structural Formulas B15 to B27. In particular, the Structural Formula B12 may be any one of the following Structural Formulas B15 to B27.

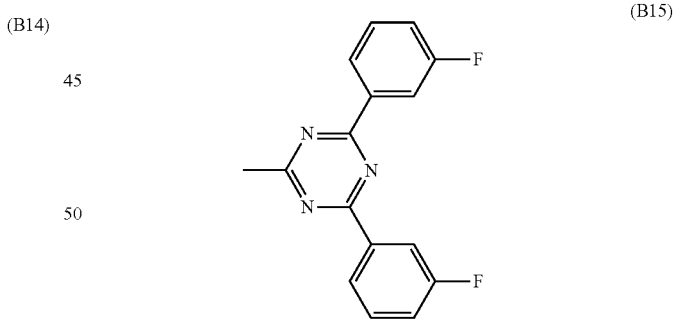
(B15)

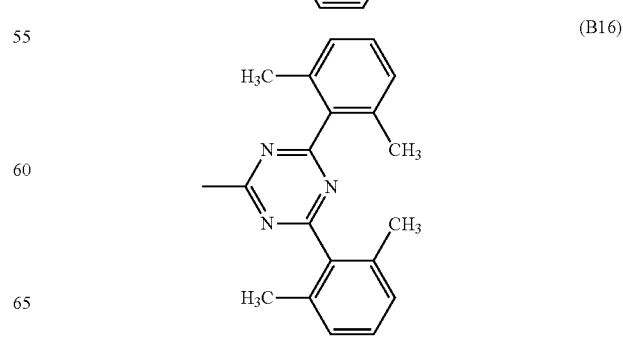
(B16)

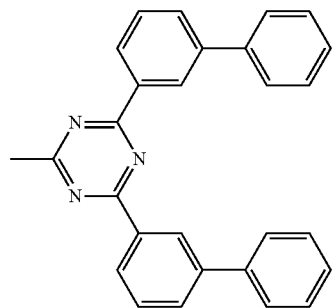 (B17)
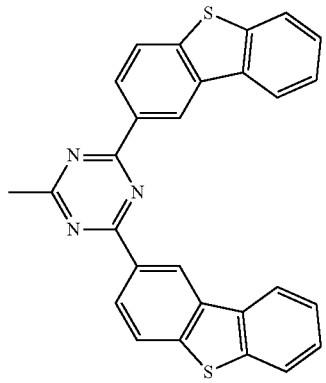 (B21)
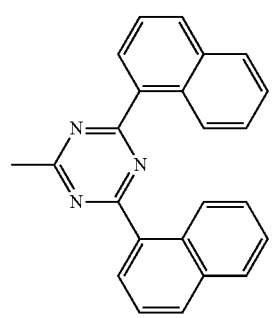 (B18)
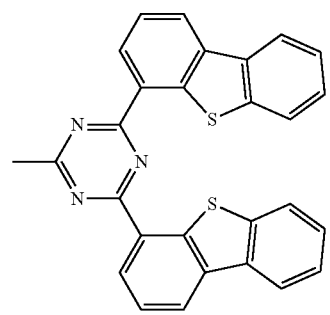 (B22)
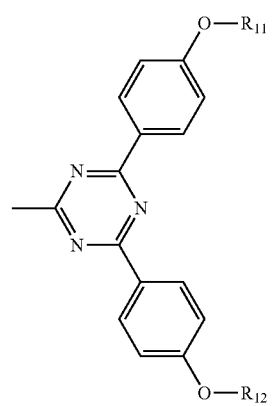 (B19)
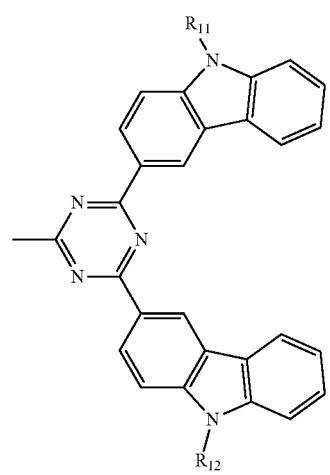 (B23)
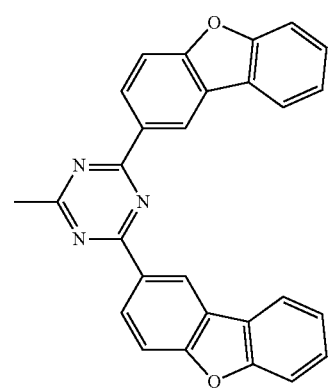 (B20)
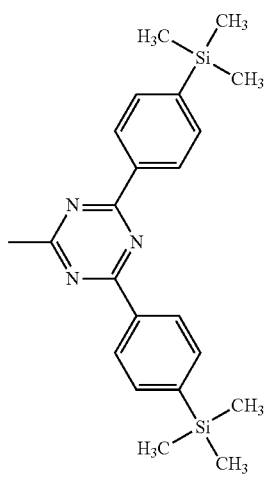 (B24)

In Structural Formulas B15 to B27,

R$_{11}$ and R$_{12}$ may be, independently of each other, hydrogen, deuterium, or a substituted or unsubstituted C1-C2 alkyl group.

Examples of the triazine group substituted with R$_{19}$ in the above Chemical Formula 3 may be the same as the following Structural Formulas B28 to B49.

-continued
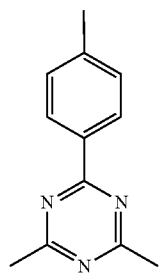 (B35)
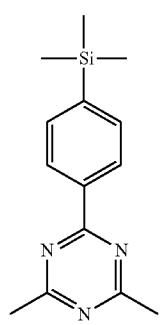 (B36)
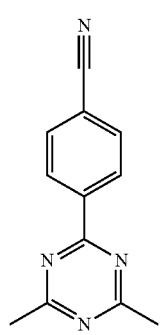 (B37)
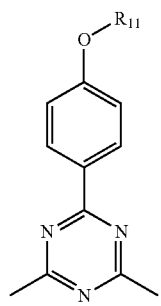 (B38)
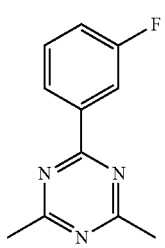 (B39)
-continued
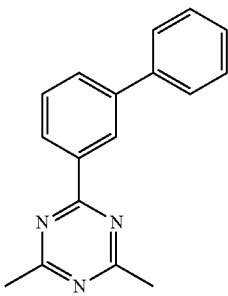 (B40)
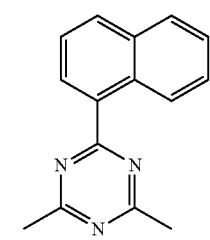 (B41)
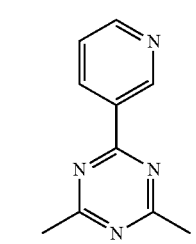 (B42)
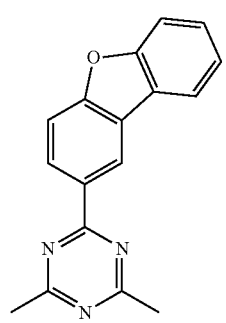 (B43)
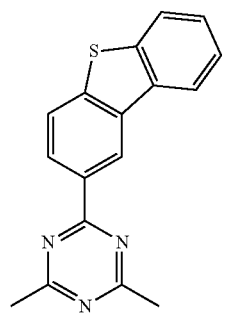 (B44)

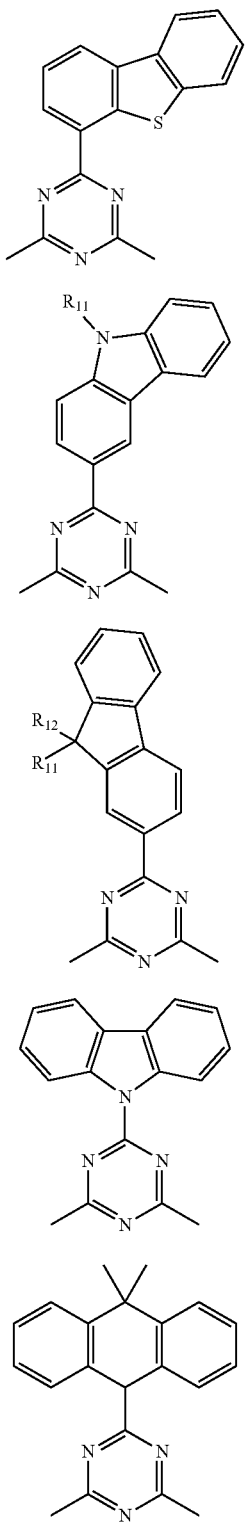

(B45)

(B46)

(B47)

(B48)

(B49)

In Structural Formulas B28 to B49, $R_{11}$ and $R_{12}$ independently represent hydrogen, deuterium, or a substituted or unsubstituted C1-C2 alkyl group.

Specific examples of the compound represented by Chemical Formula 2 may be represented by the following Chemical Formula 5, and specific examples of the compound represented by Chemical Formula 3 may be represented by the following Chemical Formula 6.

[Chemical Formula 5]

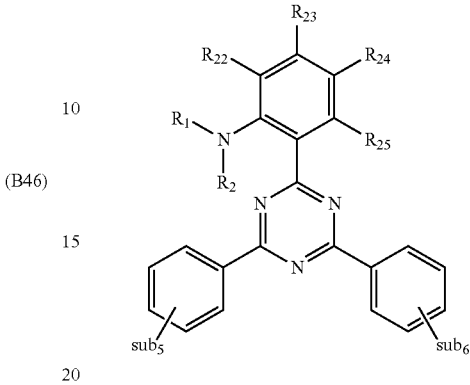

In Chemical Formula 5, $R_1$, $R_2$, and $R_{22}$ to $R_{25}$ are as defined in Chemical Formula 2, and specifically, —$NR_1R_2$ can be any one of Structural Formulas A1 to A45, for example, A6, A8, A9, or A10.

In Chemical Formula 5, $Sub_5$ and $Sub_6$ may be as defined in Structural Formula B12. As an example, at least one of $Sub_5$ and $Sub_6$ may be —$NR_eR_f$. Specifically, when either $Sub_5$ and $Sub_6$ is —$NR_eR_f$ and the —$NR_eR_f$ is located at the ortho position with respect to the triazine group, the compound of Chemical Formula 5 may be the same as the compound represented by Chemical Formula 6. When both of $Sub_5$ and $Sub_6$ are —$NR_eR_f$ and both of these —$NR_eR_f$ are located at ortho positions with respect to the triazine group, the compound of Chemical Formula 5 may be the same as the compound represented by Chemical Formula 4.

As an example, examples of the triazine group in the above Chemical Formula 5 may be the same as any of the above Structural Formula B12, and B15 to B27.

[Chemical Formula 6]

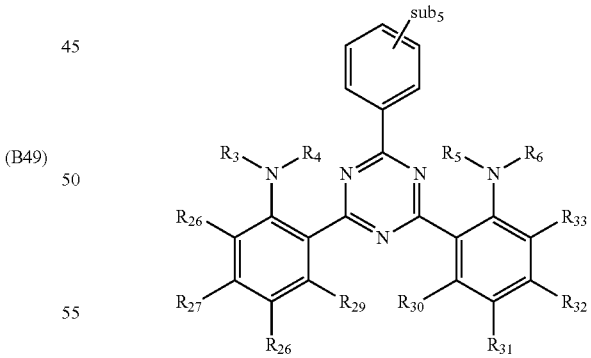

in Chemical Formula 6, $R_3$, $R_4$, $R_5$, $R_6$, $R_{26}$ to $R_{29}$, and $R_{30}$ to $R_{33}$ are as defined in Chemical Formula 3 above. Specifically, the $NR_3R_4$ and $NR_5R_6$ may, regardless of each other, be any of Structural Formulas A1 to A45, for example, A6, A8, A9, or A10.

In Chemical Formula 6, $Sub_5$ is the same as defined in Structural Formula B11. As an example, examples of the triazine group in the above Chemical Formula 6 may be the same as any of the above Structural Formulas B34 to B47.

Specific examples of the compound represented by Chemical Formula 2 may be represented by any one of the following Chemical Formulas 7 to 10.

[Chemical Formula 7]

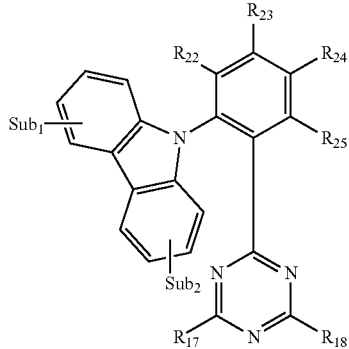

[Chemical Formula 8]

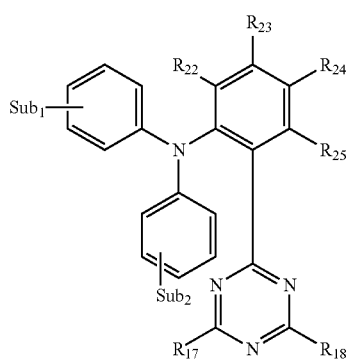

[Chemical Formula 9]

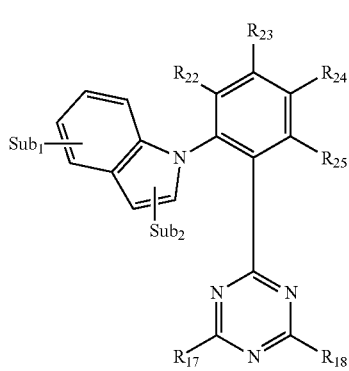

[Chemical Formula 10]

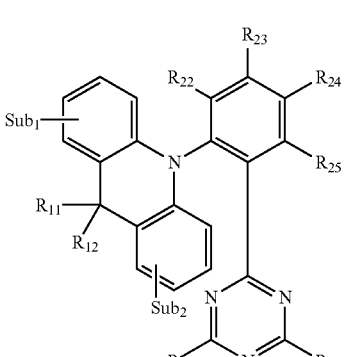

Specific examples of the compound represented by Chemical Formula 3 may be represented by the following Chemical Formula 11.

[Chemical Formula 11]

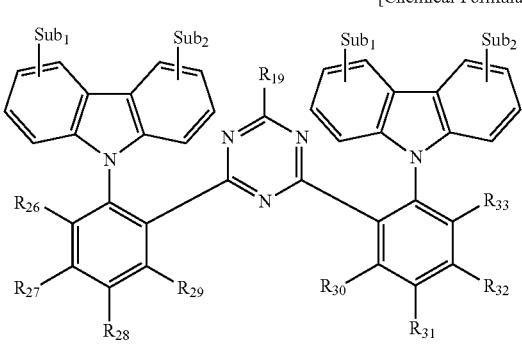

Specific examples of the compound represented by Chemical Formula 4 may be represented by the following Chemical Formula 12.

[Chemical Formula 12]

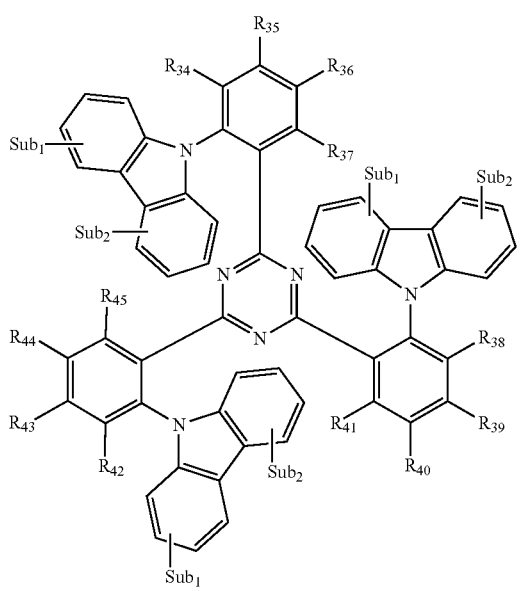

$Sub_1$ and $Sub_2$ of the above Chemical Formulas 7, 11, and 12 may be as defined in Structural Formula A9. As an example, the carbazole group including $Sub_1$ and $Sub_2$ in the above Chemical Formulas 7, 11 and 12 may be any one of the above Structural Formulas A20 to A38. $Sub_1$ and $Sub_2$ of Chemical Formula 8 may be as defined in Structural Formula A8. $Sub_1$ and $Sub_2$ in Chemical Formula 9 may be as defined in Structural Formula A6. $Sub_1$ and $Sub_2$ of Chemical Formula 10 may be as defined in Structural Formula A10. As an example, the acridane group containing $Sub_1$ and $Sub_2$ in Chemical Formula 10 may be any of Structural Formula A39 to A45.

In the above Chemical Formulas 7 to 10, $R_{17}$ and $R_{18}$ may be as defined in the above Chemical Formula 2. As an example, the triazine group including $R_{17}$ to $R_{18}$ may be any of the above-mentioned Structural Formulas B1 to B27. In particular, the triazine group containing $R_{17}$ to $R_{18}$ may be the above-mentioned Structural Formula B12, and specifically, it may be any of the above-mentioned Structural formulas B15 to B27. In the Chemical Formula 11, $R_{19}$ may be the same as defined in the Chemical Formula 3. As another example, the triazine group containing $R_{19}$ may be any of the above Structural Formulas B28 to B49.

In the Chemical Formulas 7 to 12, $R_{22}$ to $R_{45}$ may be, independently of each other, the same as any one of $R_5$ to $R_8$ defined in the above Chemical Formula 1, but specifically, $R_{22}$ to $R_{45}$ independently represent hydrogen, deuterium, a halogen group, a substituted or unsubstituted C4-C6 aryl group, or a substituted or unsubstituted C1-C3 alkyl group. Here, the substituted C1-C3 alkyl group may be a halogen-substituted C1-C3 alkyl group, and the halogen group may be F.

In the above Chemical Formula 10, $R_{11}$ and $R_{12}$ may, regardless of each other, be hydrogen, deuterium, or a substituted or unsubstituted C1-C2 alkyl group.

The thermally activated delayed fluorescent material can implement red, green, and blue luminescent colors by appropriate introduction of the electron donating group and the electron withdrawing group and reduce the difference between the singlet energy and the triplet energy to 0.3 eV or less.

Specific compounds of such thermally activated delayed fluorescent materials are represented by the following Compounds 1 to 92, but are not limited thereto.

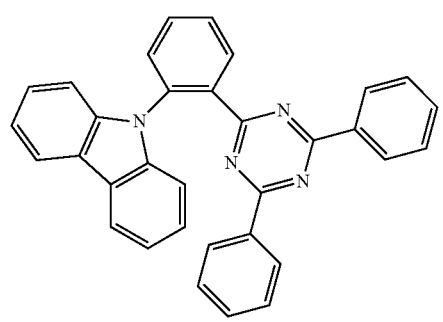

(1)

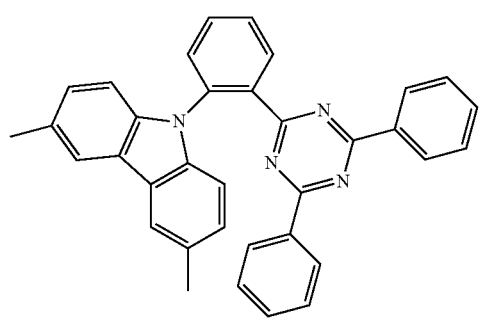

(2)

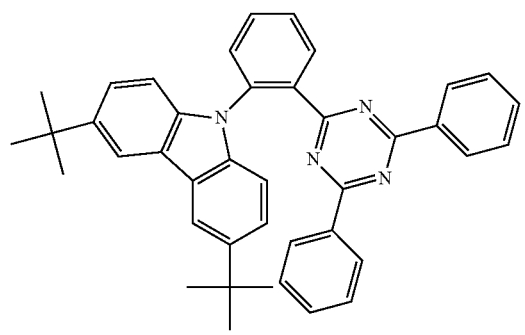

(3)

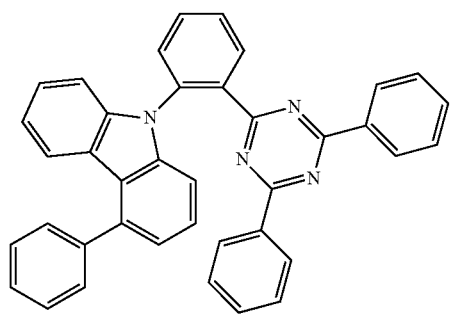

(4)

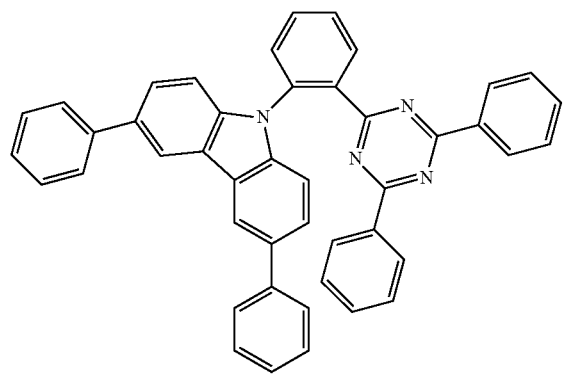

(5)

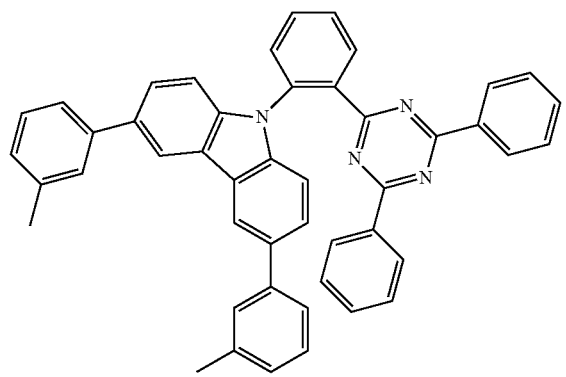

(6)

-continued
(7)
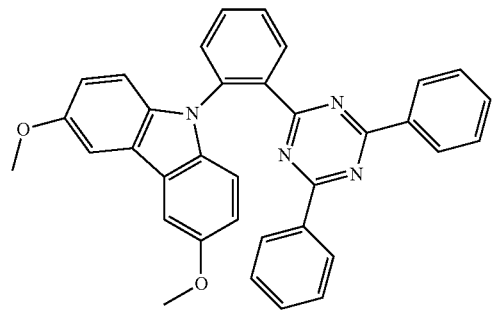
(8)
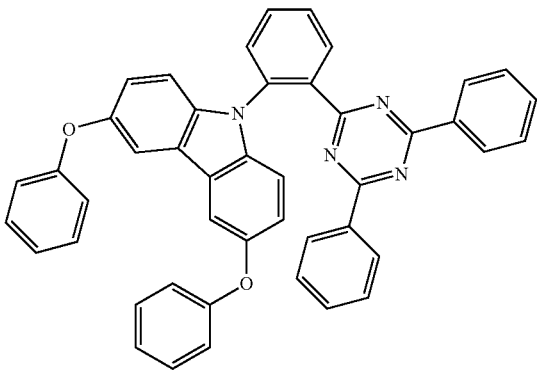
(9)
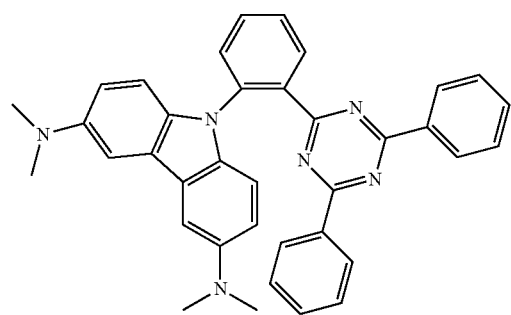
(10)
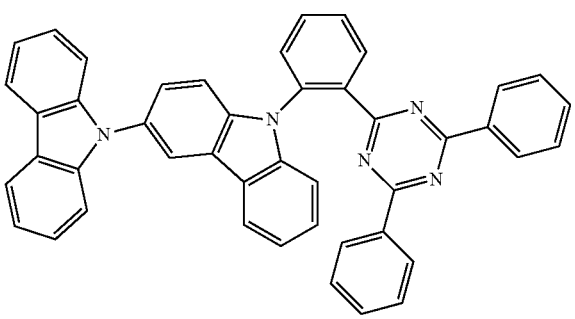
(11)
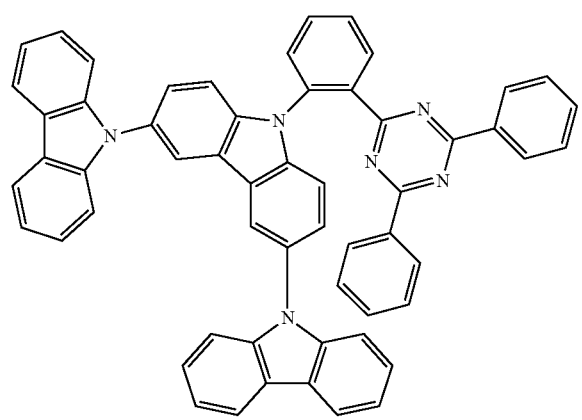
(12)
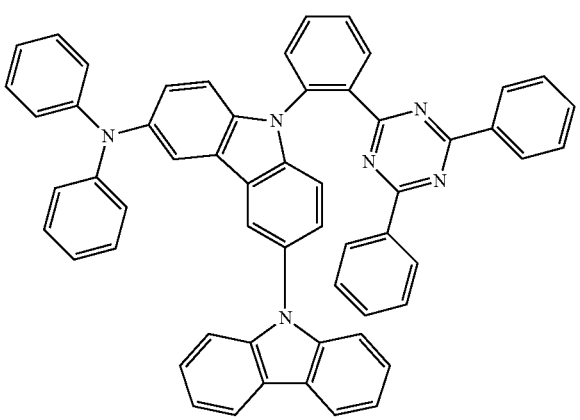
(13)
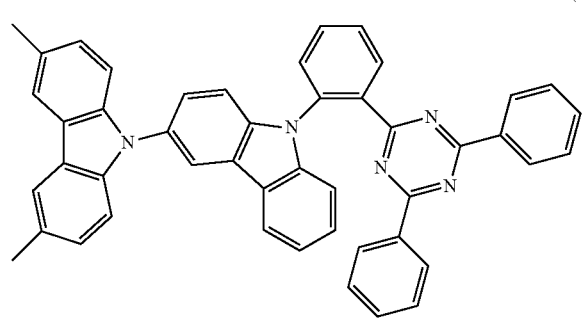
(14)
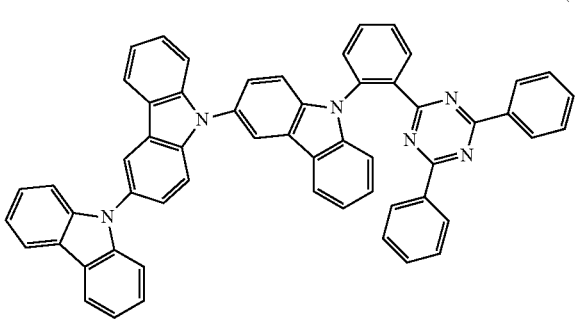

-continued
(15)
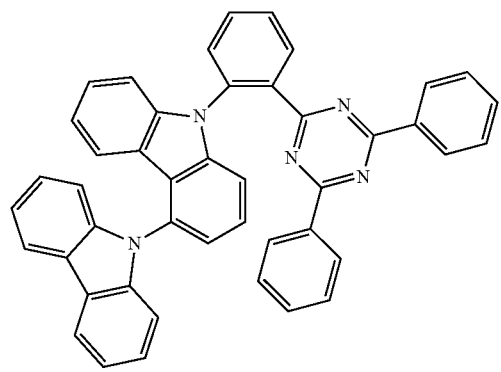
(16)
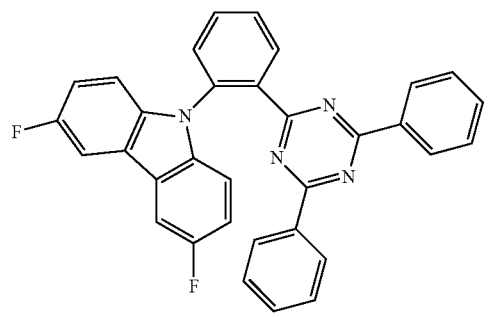
(17)
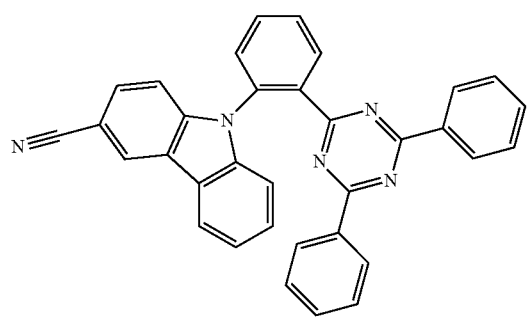
(18)
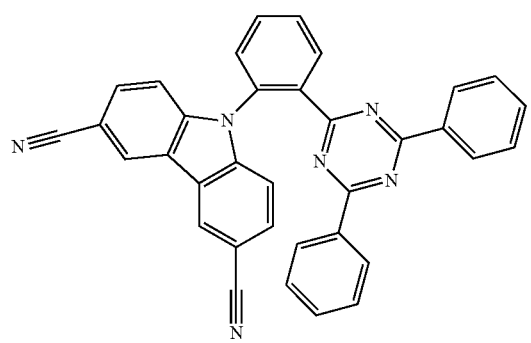
(19)
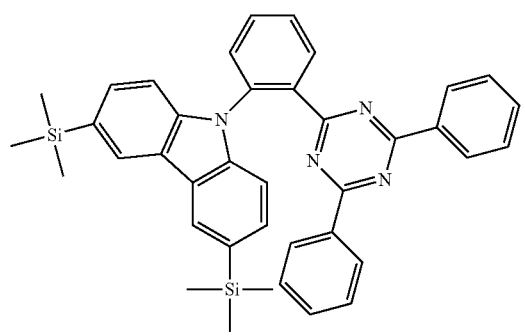
(20)
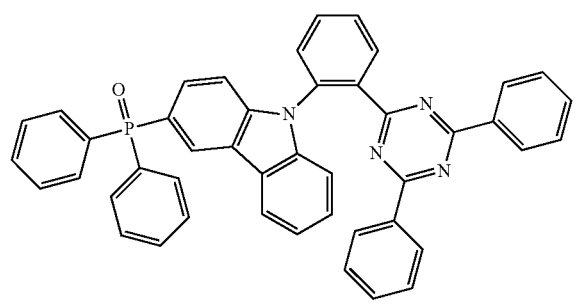
(21)
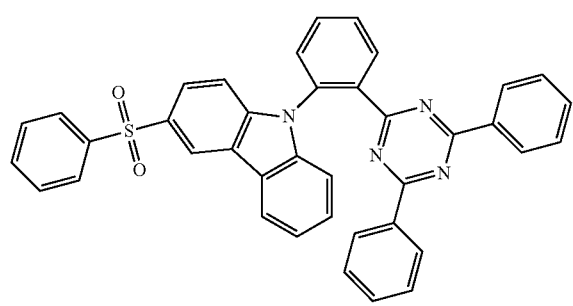
(22)
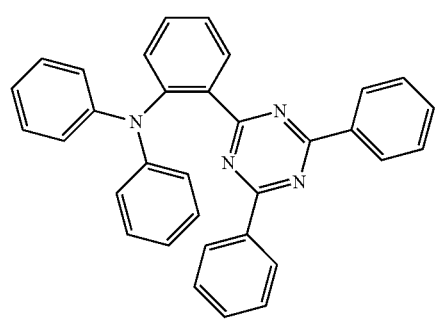

-continued
(23)
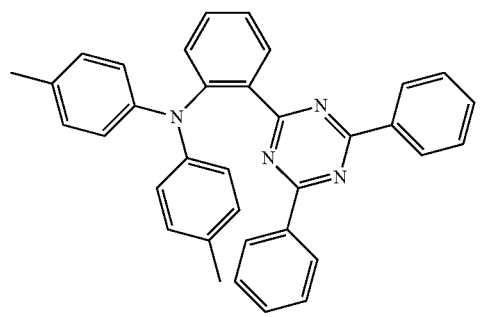
(24)
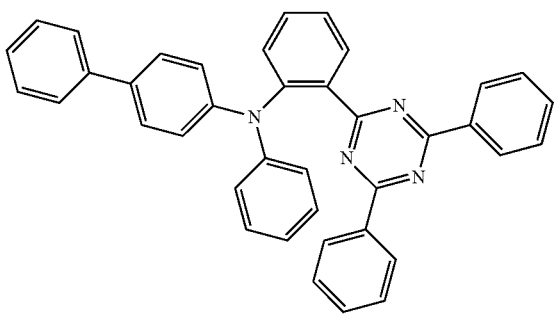
(25)
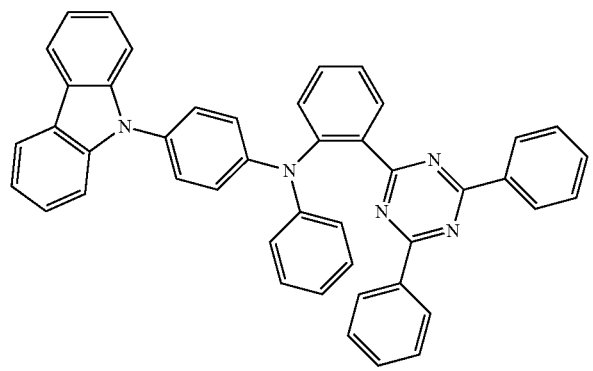
(26)
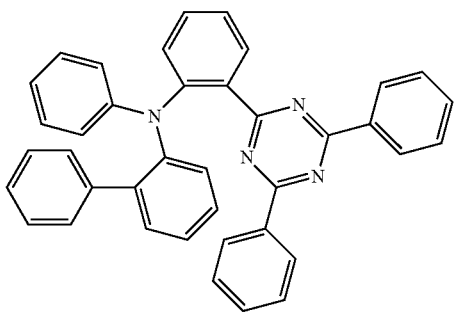
(27)
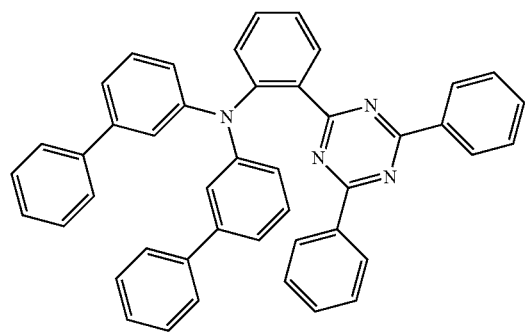
(28)
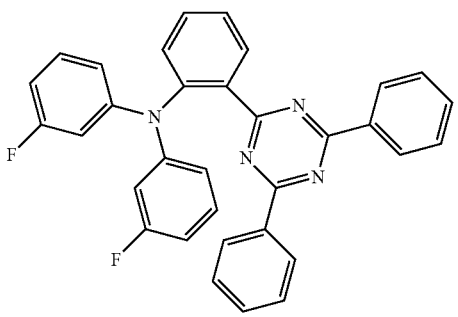
(29)
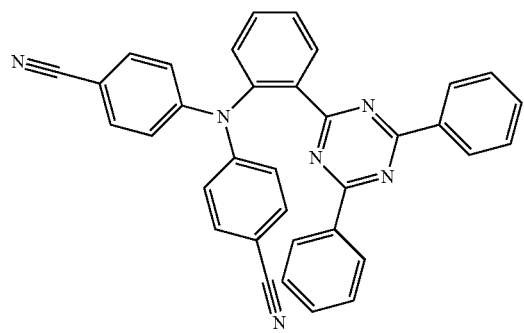
(30)
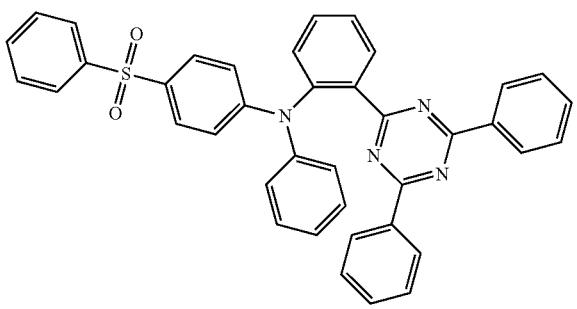

-continued
(31)
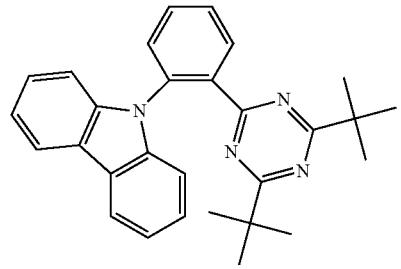
(32)
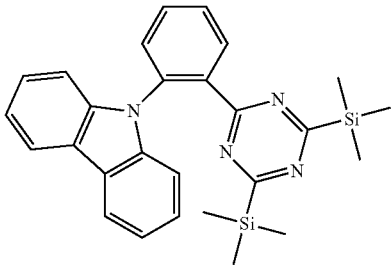
(33)
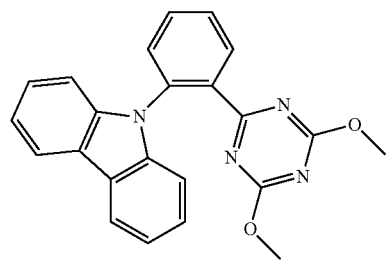
(34)
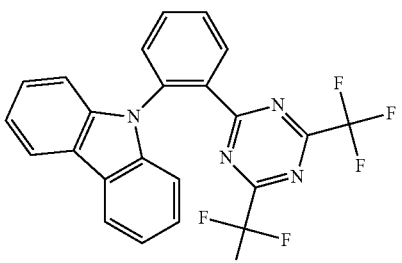
(35)
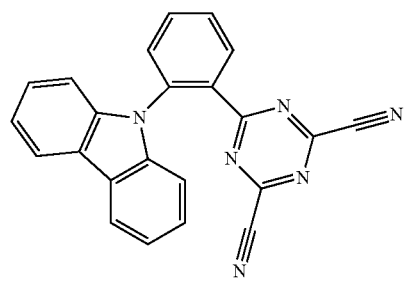
(36)
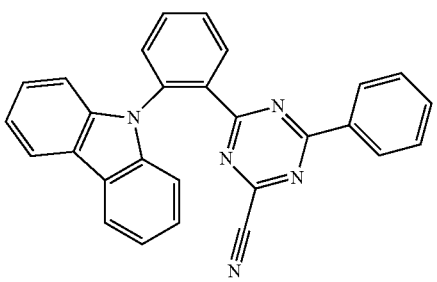
(37)
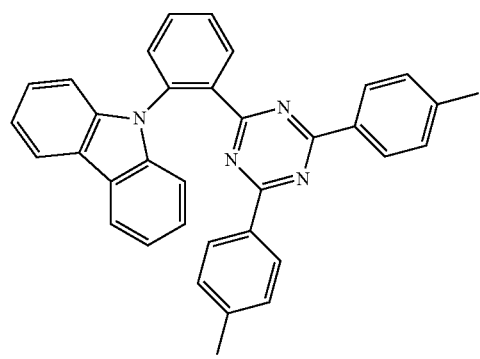
(38)
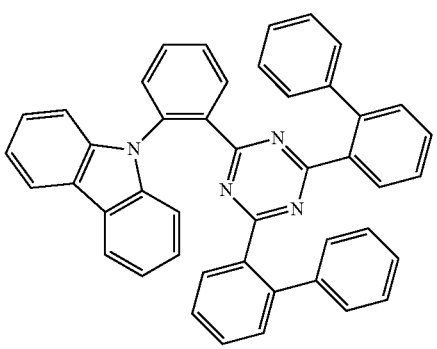
(39)
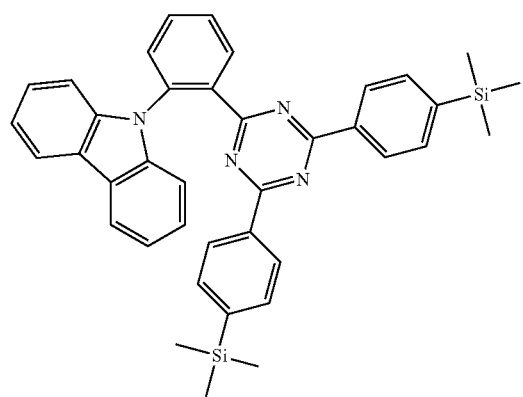
(40)
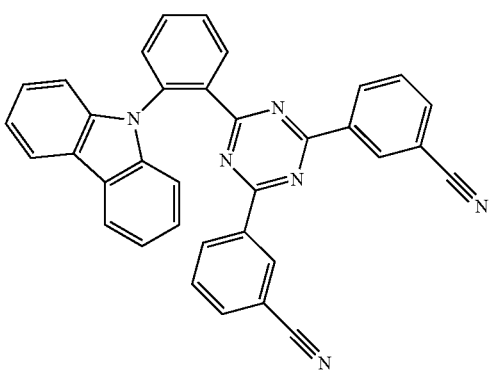

-continued
(41) 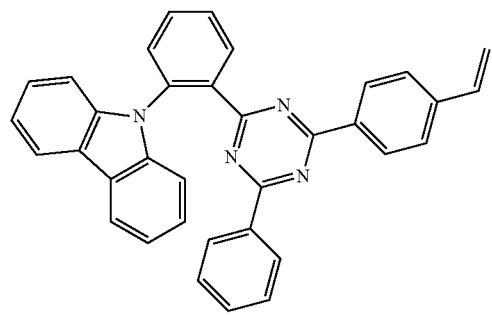
(42) 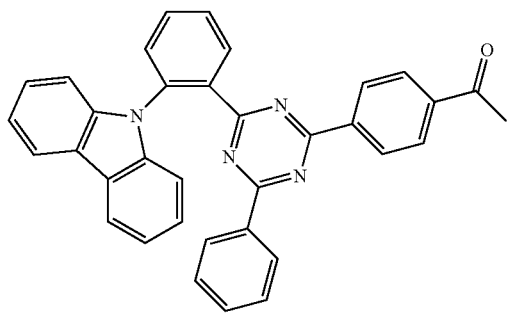
(43) 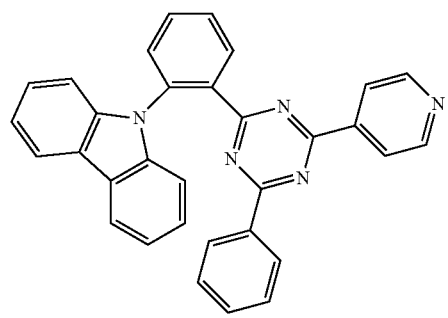
(44) 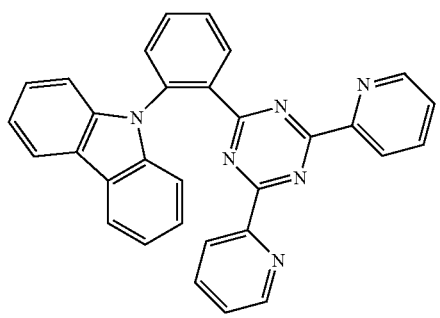
(45) 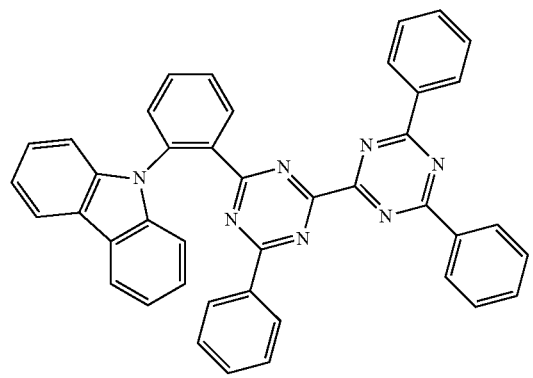
(46) 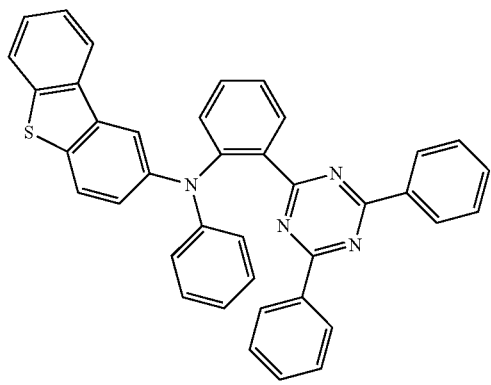
(47) 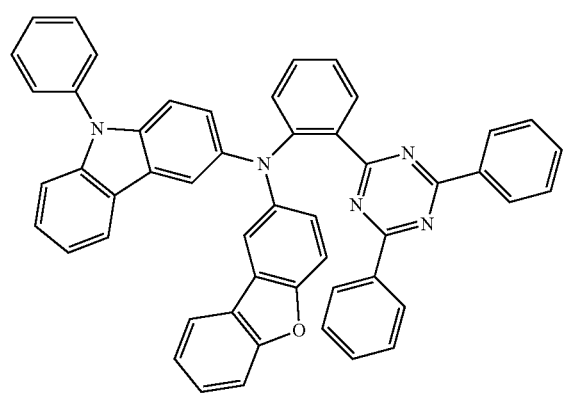
(48) 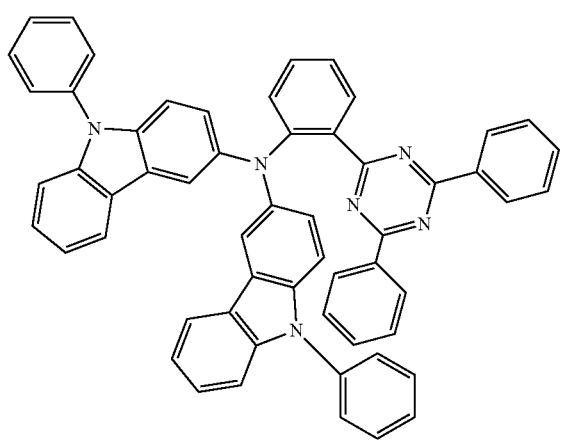

(49) 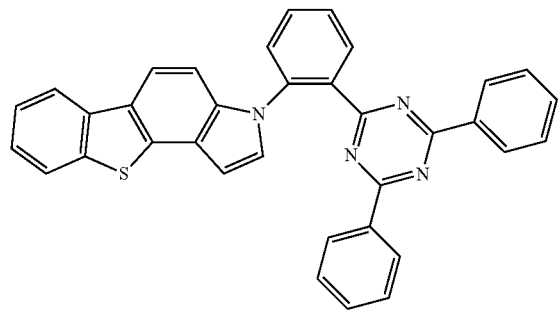
(50) 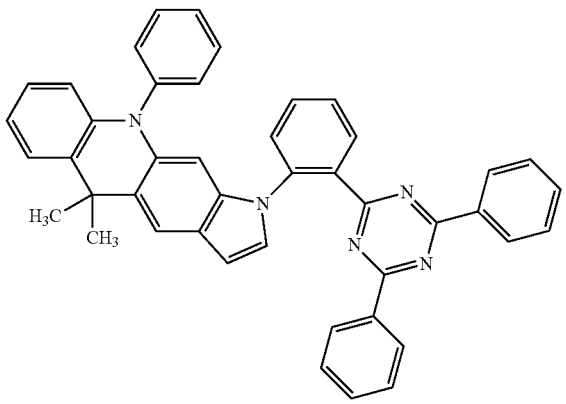
(51) 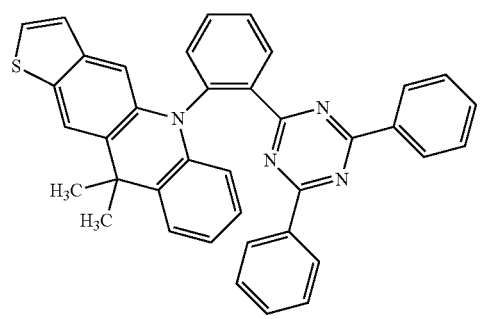
(52) 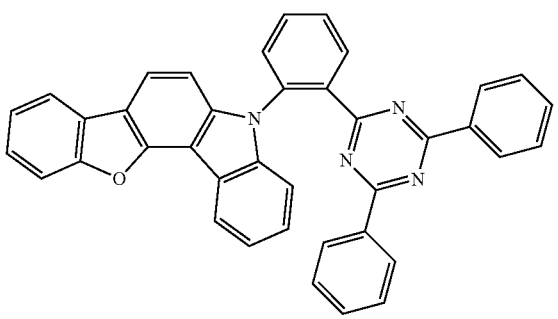
(53) 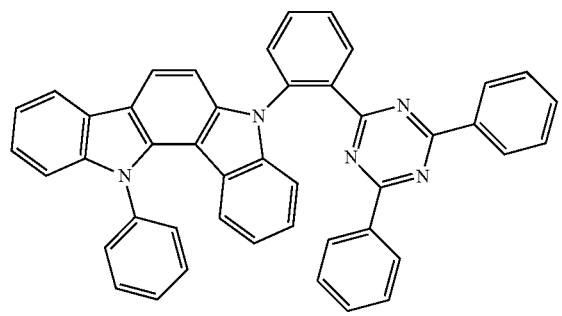
(54) 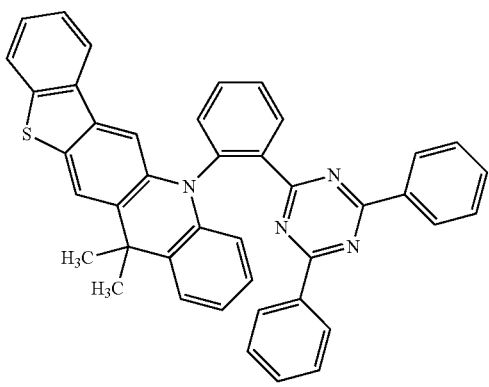
(55) 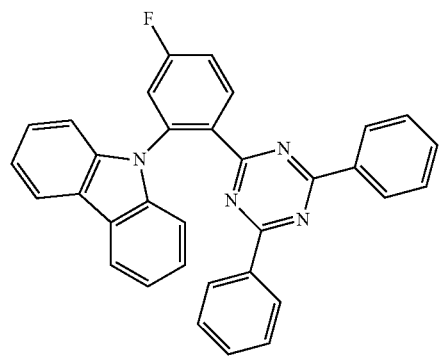
(56) 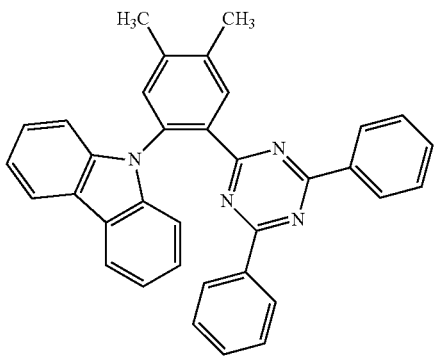

-continued
(57)
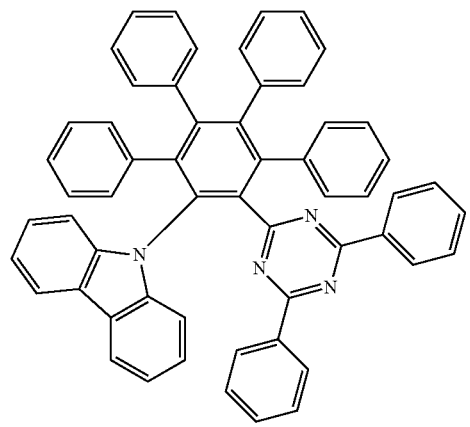
(58)
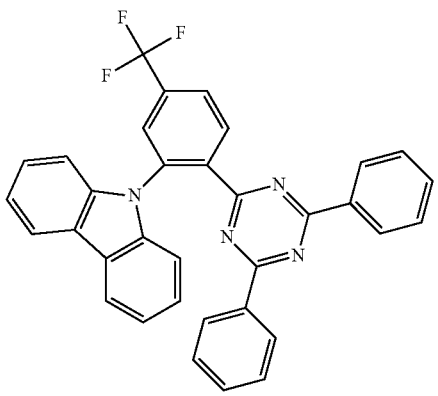
(59)
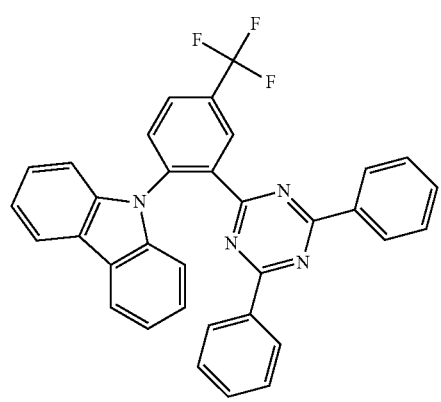
(60)
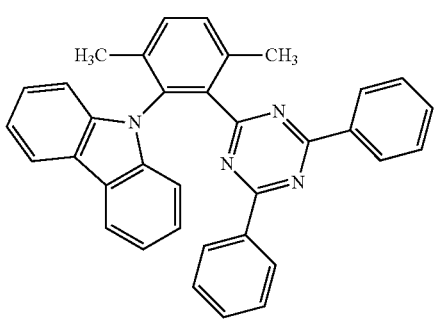
(61)
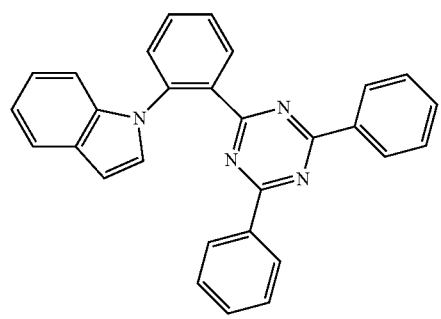
(62)
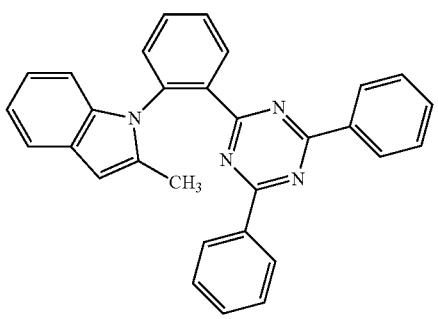
(63)
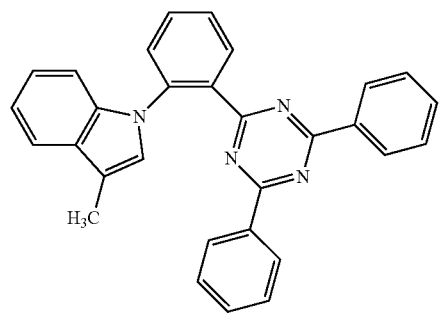
(64)
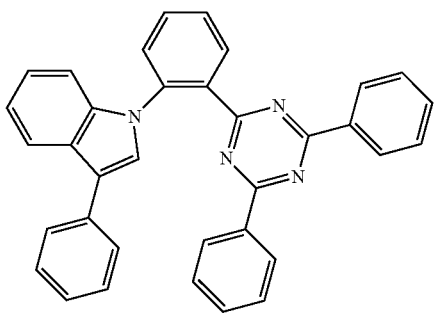

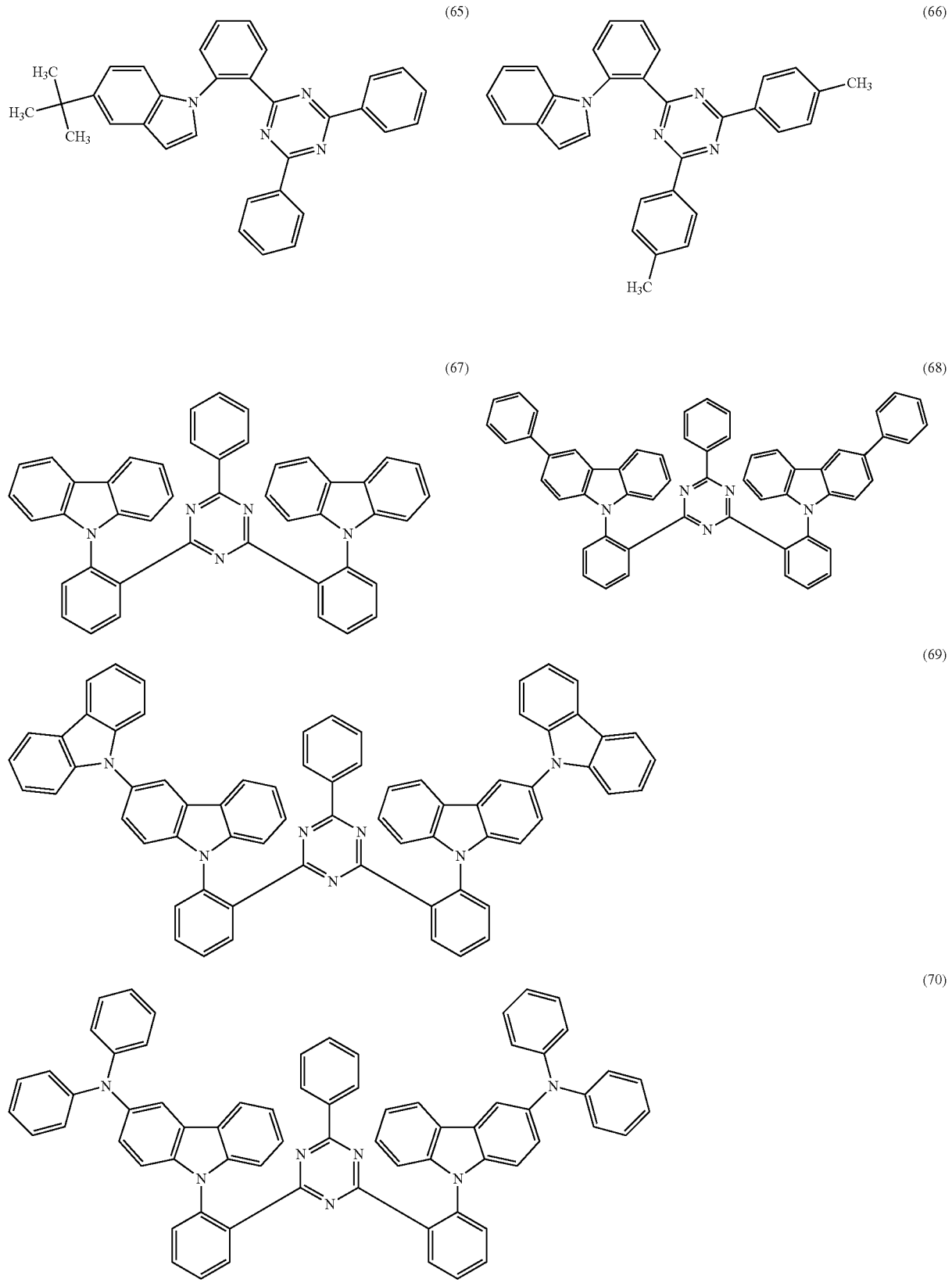

(71)
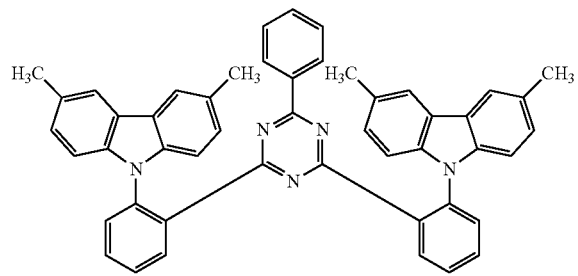
(72)
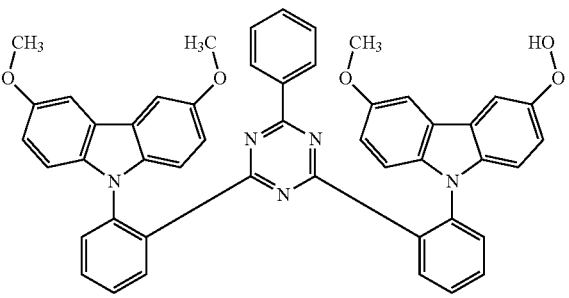
(73)
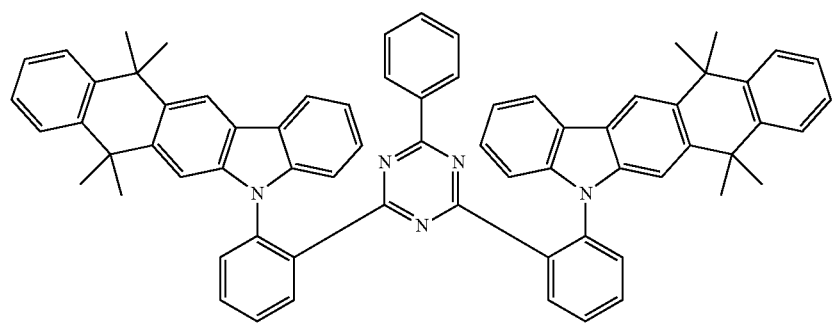
(74)
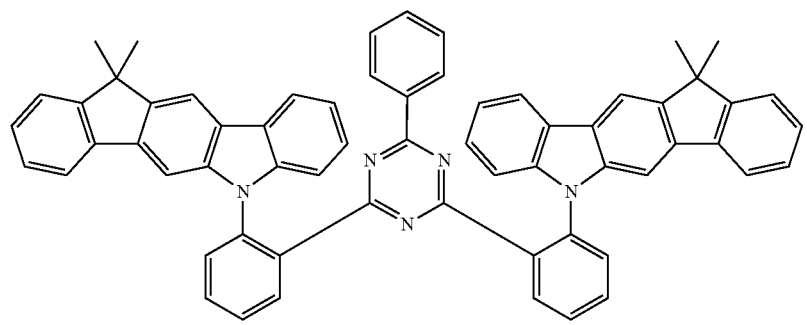
(75)
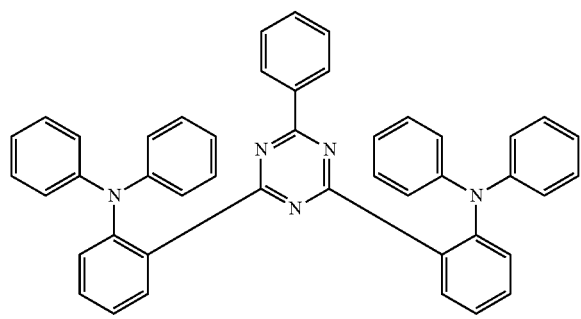
(76)
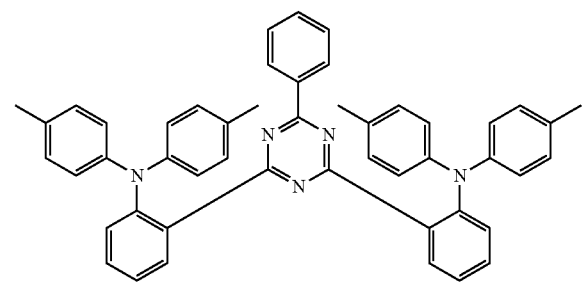

(77)
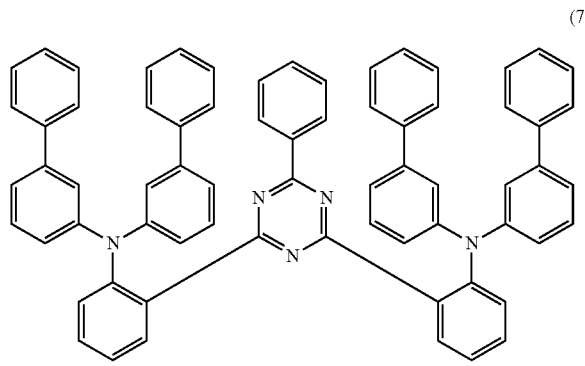
(78)
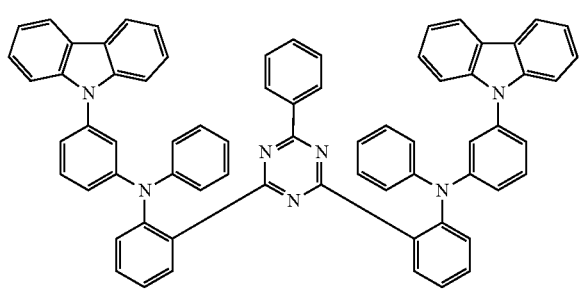
(79)
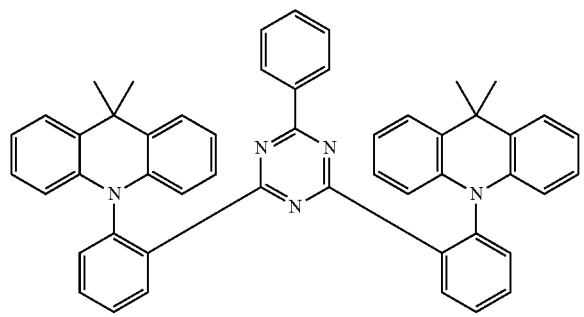
(80)
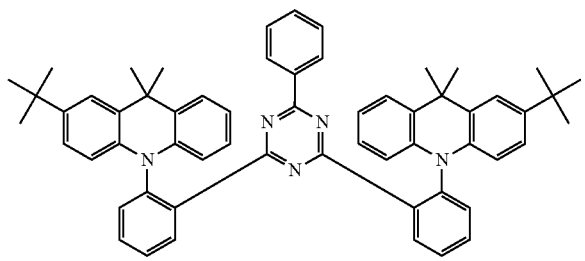
(81)
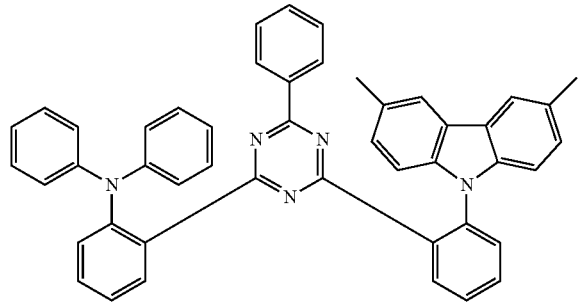
(82)
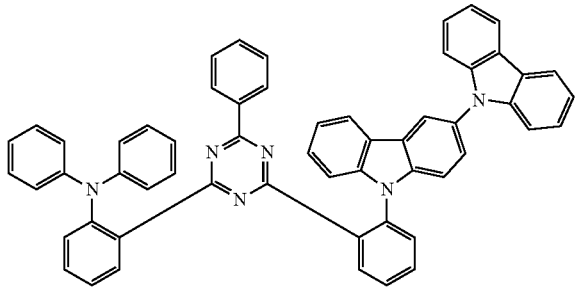
(83)
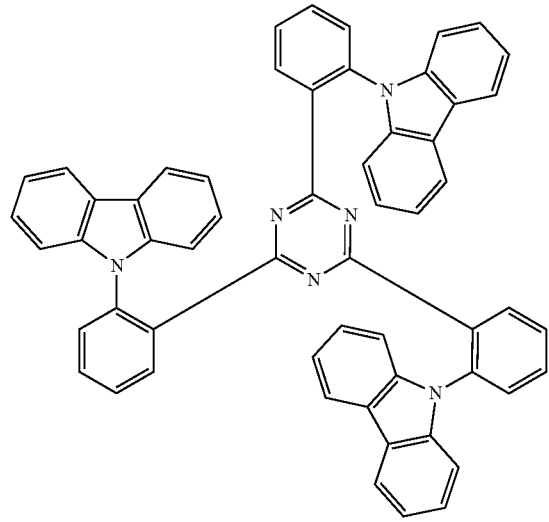
(84)
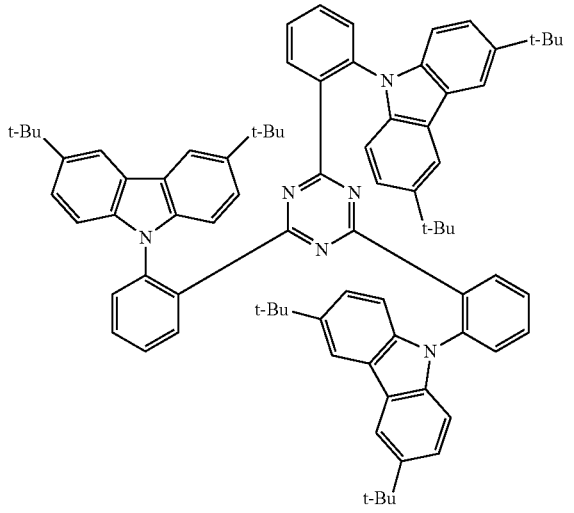

-continued
(85)
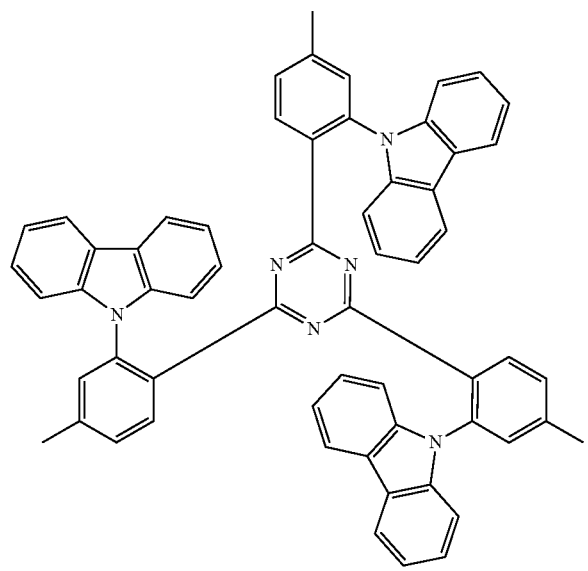
(86)
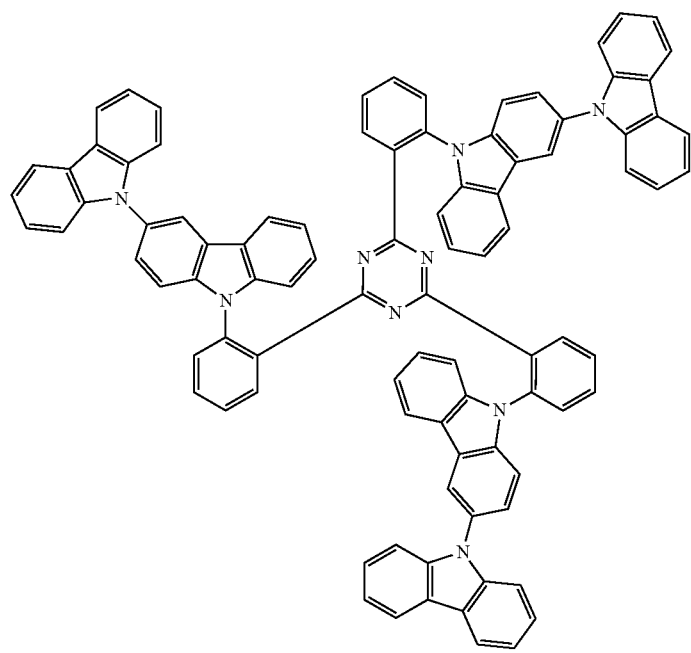
(87)
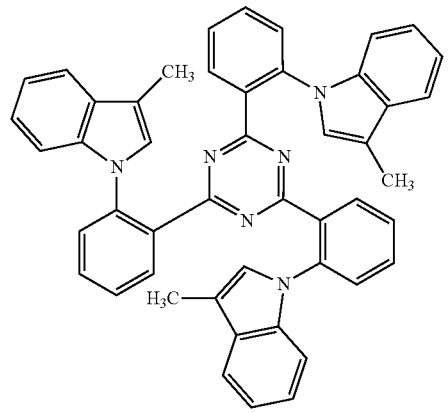
(88)
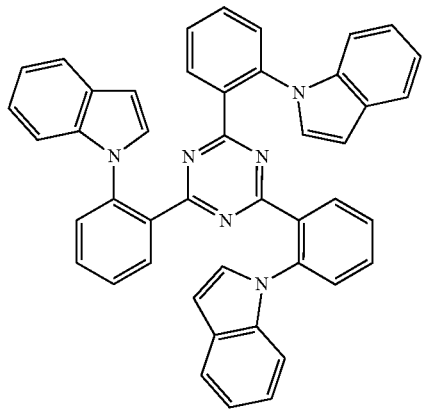

-continued

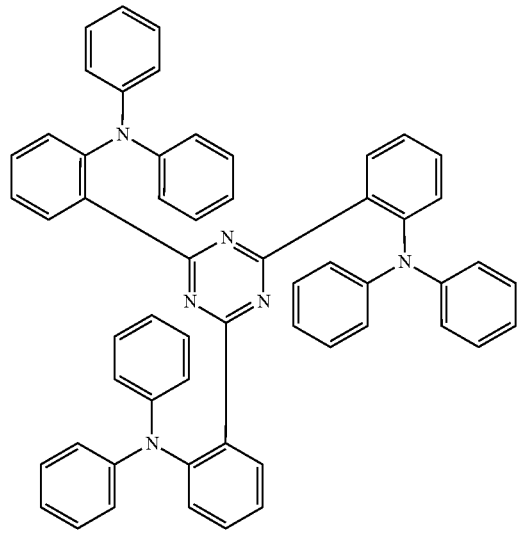

(89)

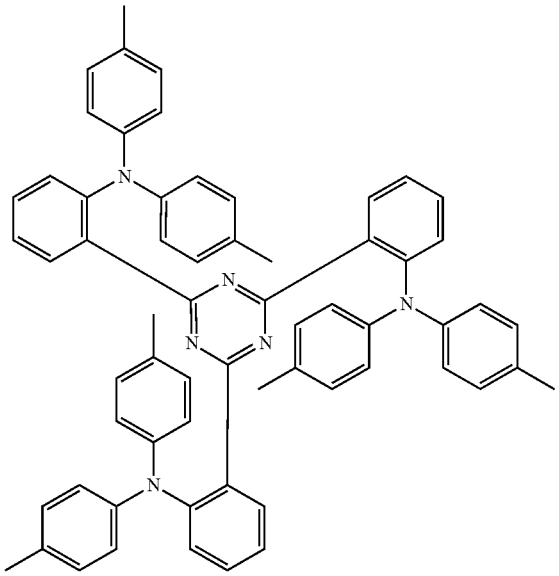

(90)

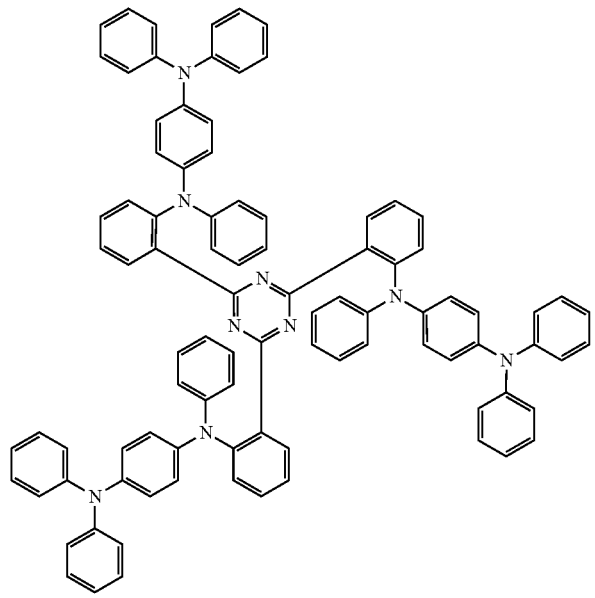

(91)

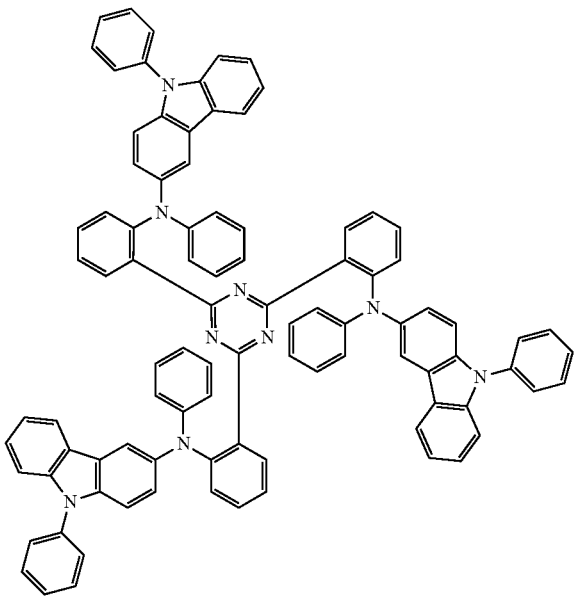

(92)

Compounds 1-21, 31-45, 52, 53, 55-60, 67-74, and 81-86 may be examples of the compounds shown in Chemical Formula 7, Compounds 22-30, 46-48, 75-78, and 89-92 may be examples of the compounds shown in Chemical Formula 8, Compounds 49, 50, 61-66, 87, and 88 may be examples of the compounds shown in Chemical Formula 9, Compounds 51, 54, 79, and 80 may be examples of the compounds shown in Chemical Formula 10, Compounds 67-74 may be examples of the compounds shown in Chemical Formula 11, and Compounds 83-86 may be examples of the compounds shown in Chemical Formula 12.

Organic Light Emitting Diode

FIG. 1 is a cross-sectional view illustrating an organic light emitting diode according to an exemplary embodiment of the present invention.

Referring to FIG. 1, an organic light emitting diode includes an anode 10, a cathode 70, a light emitting layer 40 disposed between the two electrodes, a hole conduction layer 20 disposed between the anode 10 and the light emitting layer 40, and an electron conduction layer 50 disposed between the light emitting layer 40 and the cathode 70. The hole conduction layer 20 may include a hole transport layer 25 for transporting holes and a hole injection layer 23 for facilitating injection of holes. The electron conduction layer 50 may include an electron transport layer 55 for transporting electrons and an electron injection layer 53 for facilitating injection of electrons. In addition, a hole blocking layer (not shown) may be disposed between the light emitting layer 40 and the electron transporting layer 55. Further, an electron blocking layer (not shown) may be disposed between the light emitting layer 40 and the hole transporting layer 25. However, it is not limited thereto, and the electron transport layer 55 may serve as the hole blocking layer, or the hole transport layer 25 may serve as the electron blocking layer.

When a forward bias is applied to the organic light emitting diode, holes are injected into the light emitting layer 40 from the anode 10, and electrons are injected into the light emitting layer 40 from the cathode 70. Electrons and holes injected into the light emitting layer 40 are combined to form excitons, and light is emitted while the excitons transition to the ground state.

The light emitting layer 40 may be made of a single light emitting material, or may include a host material and a dopant material. The single light emitting material or the light emitting dopant material may be a compound represented by any one of the above-described Chemical Formulas 1 to 12 and Compounds 1 to 92, specifically, a thermally activated delayed fluorescent material. In this case, the efficiency of the organic light emitting diode can be greatly improved. The thermally activated delayed fluorescent material has a form in which an electron donating group and an electron withdrawing group are connected to benzene and the electron withdrawing group is positioned in an ortho position to the electron donating group. Thus, the difference between singlet energy and triplet energy can be reduced to less than 0.3 eV. The thermally activated delayed fluorescent material can more efficiently facilitate transition from the triplet excited state to the singlet excited state by heat (at room temperature or element operating temperature), thereby improving the quantum efficiency. In addition, various combinations of the red, green, and blue luminescent colors can be realized by the appropriate introduction of the electron donating group and the electron withdrawing group.

The host material may be selected from the group consisting of mCP (N,N-dicarbazolyl-3,5-benzene), Alq3, CBP (4,4'-N,N'-dicarbazole-biphenyl), 9,10-di(naphthalen-2-yl) anthracene, TPBI (1,3,5-tris(N-phenylbenzimidazole-2-yl) benzene), TBADN (3-tert-butyl-9,10-di(naphth-2-yl)anthracene), E3 (see the following formula), and BeBq2 (see the following formula).

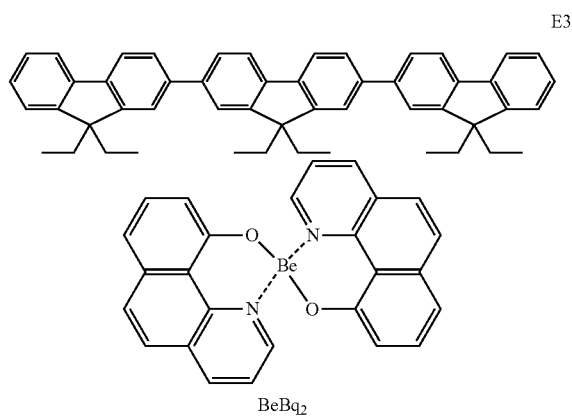

BeBq₂

Meanwhile, the hole injection layer 23 and/or the hole transport layer 25 are layers having a HOMO level between the work function level of the anode 10 and the HOMO level of the light emitting layer 40, and has the function of enhancing the injection or transport efficiency of holes from the anode 10 to the light emitting layer 40. The electron injection layer 53 and/or the electron transport layer 55 are layers having a LUMO level between the work function level of the cathode 70 and the LUMO level of the light emitting layer 40, and has the function of enhancing the injection or transport efficiency of electrons from the cathode 70 to the light emitting layer 40.

The anode 10 may be a conductive metal oxide, a metal, a metal alloy, or a carbon material. The conductive metal oxide may be at least one selected from the group consisting of indium tin oxide (ITO), fluorine tin oxide (FTO), antimony tin oxide (ATO), SnO2, ZnO, or any combination thereof. The metal or metal alloy suitable as the anode 10 may be Au or CuI. The carbon material may be graphite, graphene, or carbon nanotubes.

The hole injecting layer 23 or the hole transporting layer 25 may include a material commonly used as a hole transporting material, and one layer may have a different hole transporting materials or a different hole transporting material layers. The hole transporting material may be, for example, mCP (N,N-dicarbazolyl-3,5-benzene); PEDOT: PSS (poly(3,4-ethylenedioxythiophene):polystyrenesulfonate); NPD (N,N'-di(1-naphthyl)-N,N'-diphenylbenzidine); N,N'-diphenyl-N,N'-di(3-methylphenyl)-4,4'-diaminobiphenyl (TPD); N,N'-diphenyl-N,N'-dinaphthyl-4, 4'-diaminobiphenyl; N,N,N',N'-tetra-p-tolyl-4,4'-diaminobiphenyl; N,N,N',N'-tetraphenyl-4,4'-diaminobiphenyl; porphyrin compound derivatives such as copper (II) 1,10,15,20-tetraphenyl-21H,23H-porphyrin and the like; TAPC (1,1-bis[4-[N,N'-di(p-tolyl)amino]phenyl] cyclohexane); triarylamine derivatives such as N,N,N-tri(p-tolyl)amine and 4,4',4'-tris[N-(3-methylphenyl)-N-phenylamino]triphenylamine; carbazole derivatives such as N-phenylcarbazole and polyvinylcarbazole; phthalocyanine derivatives such as metal-free phthalocyanine and copper phthalocyanine; starburst amine derivatives; enamine stilbene derivatives; derivatives of aromatic tertiary amine and styrylamine compounds; polysilane; and the like. Such a hole transporting material may also serve as the electron blocking layer.

The hole blocking layer serves to prevent triplet excitons or holes from diffusing toward the cathode 70, and may be arbitrarily selected from known hole blocking materials. For example, oxadiazole derivatives, triazole derivatives, phenanthroline derivatives and the like can be used.

The electron transporting layer 55 may be formed of a material selected from the group consisting of TSPO1 (diphenylphosphine oxide-4-(triphenylsilyl)phenyl), tris(8-quinolinolate) aluminum (Alq3), 2,5-diarylsilole derivative (PyPySPyPy), perfluorinated compound (PF-6P), COTs (octasubstituted cyclooctatetraene), TAZ (see the following Chemical Formula), Bphen (4,7-diphenyl-1,10-phenanthroline), BCP (see the following formula), and BAlq (see the following formula).

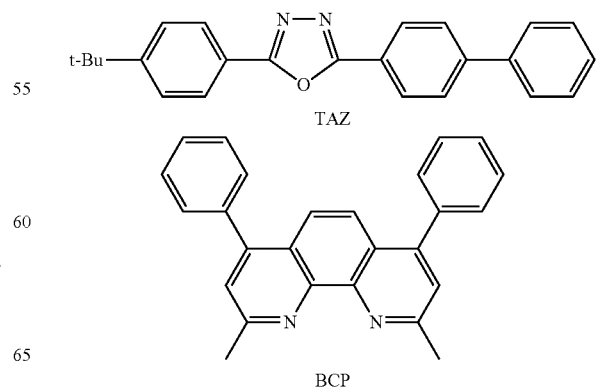

-continued

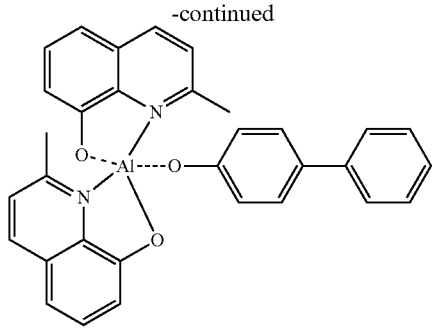

BAlq

The electron injection layer 53 may be, for example, LiF, NaCl, CsF, Li2O, BaO, BaF2, or Liq (lithium quinolate).

The cathode 70 is a conductive film having a lower work function than the anode 70 and is made of a metal such as aluminum, magnesium, calcium, sodium, potassium, indium, yttrium, lithium, silver, lead, cesium, or the like, or a combination of two or more species among those metals.

The anode 10 and the cathode 70 may be formed using a sputtering method, a vapor deposition method, or an ion beam deposition method. The hole injecting layer 23, the hole transporting layer 25, the light emitting layer 40, the hole blocking layer, the electron transporting layer 55 and the electron injecting layer 53 are, regardless of each other, formed by evaporation or coating methods such as spraying, spin coating, dipping, printing, doctor blading, or electrophoresis.

The organic light emitting diode may be disposed on a substrate (not shown), which may be disposed below the anode 10 or above the cathode 70. In other words, the anode 10 may be formed on the substrate before the cathode 70, or the cathode 70 may be formed before the anode 10.

The substrate may be a light-transmissive substrate as a flat plate member, in which case the substrate may be glass; ceramics; or a polymer material such as polycarbonate (PC), polyethylene terephthalate (PET), polyethylene naphthalate (PEN), polyimide (PI), polypropylene (PP). However, the present invention is not limited to this, and the substrate may be a metal substrate capable of light reflection.

Hereinafter, exemplary embodiments of the present invention will be described in order to facilitate understanding of the present invention. It should be understood, however, that the following examples are for the purpose of promoting understanding of the present invention and are not intended to limit the scope of the present invention.

EXAMPLES

Scheme 1

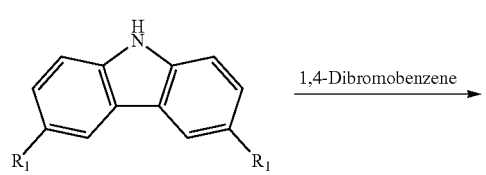

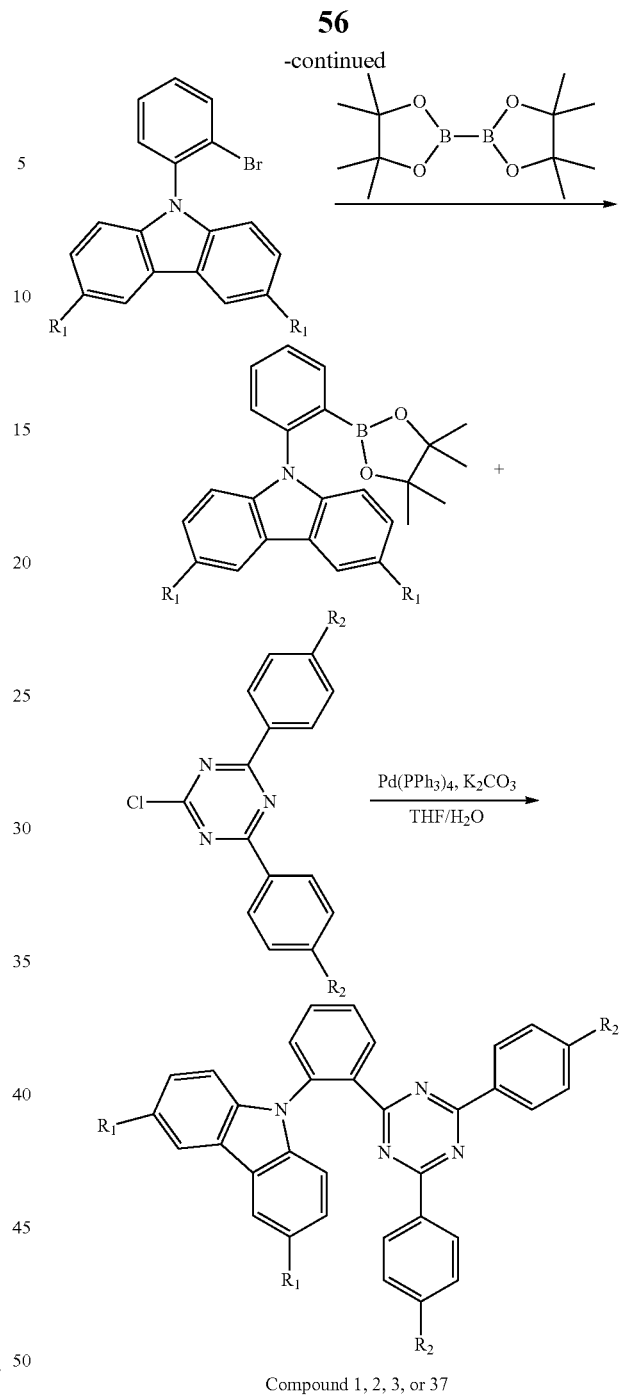

Compound 1, 2, 3, or 37

In Scheme 1, the product is Compound 1 when both of $R_1$ and $R_2$ are hydrogen, Compound 2 when $R_1$ is a methyl group and $R_2$ is hydrogen, Compound 3 when $R_1$ is a t-butyl group and $R_2$ is hydrogen, and Compound 37 when $R_1$ is hydrogen and $R_2$ is a methyl group.

Synthesis Example 1: Synthesis of Compound 1

Step 1:

Carbazole (10.0 g, 59.8 mmol), 1,2-dibromobenzene (21.16 g, 89.71 mmol), potassium carbonate (16.53 g, 119.61 mmol) and copper iodide (CuI) (5.69 g, 29.90 mmol) were dissolved in N,N-dimethylacetamide (250 ml) and then oxygen was removed from the solution through nitrogen bubbling. After oxygen was removed, the mixture was refluxed and stirred for 24 hours. The reaction solution was extracted with methylene chloride, and then subjected to column chromatography using a methylene chloride/hexane mixed solvent as eluent to obtain 15.99 g of 9-(2-bromophenyl)carbazole. 9-(2-bromophenyl)carbazole: Mass Spec (EI) m/z 322 [(M+H)$^+$]

Step 2:

9-(2-bromophenyl)carbazole (10 g, 31.03 mmol), 4,4,4',4',5,5,5',5'-octamethyl-2,2'-bi(1,3,2-dioxaborane) (11.82 g, 46.55 mmol), potassium acetate (9.14 g, 93.11 mmol), and 1,1'-bis(diphenylphosphino) ferrocene-palladium (II) (0.76 g, 0.93 mmol) were dissolved in 1,4-dioxane (180 ml), and then oxygen in the solution was removed through nitrogen bubbling. After oxygen was removed, the mixture was refluxed and stirred for 24 hours. The reaction solution was extracted with methylene chloride and then subjected to column chromatography using a methylene chloride/hexane mixed solvent as eluent to obtain 4.01 g of 9-(2-(4,4,5,5-tetramethyl-1,3,2-dioxaborolan-2-yl)phenyl) carbazole. 9-(2-(4,4,5,5-tetramethyl-1,3,2-dioxaborolan-2-yl) phenyl) carbazole: Mass Spec (EI) m/z 369 [(M+H)$^+$]

Step 3:

9-(2-(4,4,5,5-tetramethyl-1,3,2-dioxabolan-2-yl)phenyl) carbazole (3 g, 8.12 mmol), 2-chloro-4,6-diphenyl-1,3,5-triazine (2.61 g, 9.75 mmol), tetrakis (triphenylphosphine) palladium (0) (0.28 g, 0.24 mmol) were added to a mixed solvent of tetrahydrofuran (60 ml) and potassium carbonate 2M solution (20 ml), and then the mixture was refluxed for 24 hours. The reaction solution was extracted with methylene chloride, and then purified by column chromatography using a methylene chloride/hexane mixed solvent as eluent, and finally 3.31 g of a pure white solid was obtained through sublimation purification.

Compound 1:

yield 86%, Mass Spec (EI) m/z 474 [(M+H)$^+$]. Elemental analysis theoretical value $C_{33}H_{22}N_4$: C, 83.52%; H, 4.67%; N, 11.81%. Measured: C, 83.52%; H, 4.74%; N, 11.69%. $^1$H NMR (500 MHz, CDCl$_3$): δ 8.57 (d, 1H), 8.03 (t, 6H), 7.85 (t, 1H), 7.78 (t, 1H), 7.73 (d, 1H), 7.48 (t, 2H), 7.34 (t, 6H), 7.24~7.19 (m, 4H).

Synthesis Example 2: Synthesis of Compound 2

Compound 2 was obtained in a yield of 83% using the same method as in Synthesis Example 1 except that 3,6-dimethylcarbazole was used instead of carbazole in Step 1 of Synthesis Example 1.

Compound 2:

Mass Spec (FAB) m/z 502 [(M+H)$^+$]. Elemental analysis theoretical value $C_{35}H_{26}N_4$: C (83.64%) H (5.21%) N (11.15%) Measured: C, 83.69%; H, 5.26%; N, 11.09%. $^1$H NMR (500 MHz, CDCl$_3$): 8.50 (d, 1H), 8.00 (d, 4H), 7.78 (t, 3H), 7.73 (t, 1H), 7.67 (d, 1H), 7.47 (t, 2H), 7.31 (t, 4H), 7.11 (d, 2H), 7.06 (d, 2H), 2.49 (s, 6H).

Synthesis Example 3: Synthesis of Compound 3

Compound 3 was obtained in a yield of 81% using the same method as in Synthesis Example 1 except that 3,6-di-t-butylcarbazole was used instead of carbazole in Step 1 of Synthesis Example 1.

Compound 3:

Mass Spec (EI) m/z 586 [(M+H)$^+$]. Elemental analysis theoretical value $C_{41}H_{38}N_4$: C (83.92%) H (6.53%) N (9.55%) Measured: C, 83.85%; H, 6.61%; N, 9.53%. $^1$H NMR (500 MHz, CDCl$_3$): 8.56 (d, 1H), 8.09 (d, 4H), 8.02 (d, 2H), 7.81 (t, 1H), 7.74 (t, 1H), 7.68 (d, 1H), 7.49 (t, 2H), 7.34 (t, 6H), 7.11 (d, 2H), 1.42 (s, 18H).

Synthesis Example 4: Synthesis of Compound 37

Compound 37 was obtained in a yield of 78% using the same method as in Synthesis Example 1 except that 2-chloro-4,6-di-p-tolyl-1,3,5-triazine was used instead of 2-chloro-4,6-diphenyl-1,3,5-triazine in Step 3 of Synthesis Example 1.

Compound 37:

Mass Spec (FAB) m/z 502 [(M+H)$^+$]. Elemental analysis theoretical value $C_{35}H_{26}N_4$: C (83.64%) H (5.21%) N (11.15%) Measured: C (83.53%) H (5.27%) N (11.18%). $^1$H NMR (500 MHz, CDCl$_3$): 8.55 (d, 1H), 7.95 (d, 4H), 7.78~7.72 (m, 3H), 7.48 (t, 2H), 7.11 (d, 4H), 7.05~6.95 (m, 6H), 2.72 (s, 6H).

Synthesis Example 5: Synthesis of Compound 22

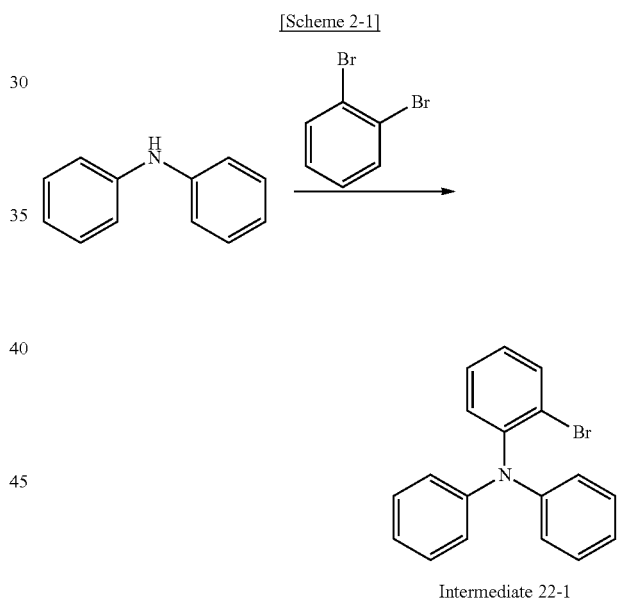

Intermediate 22-1

Step 1:

Diphenylamine (10.0 g, 59.09 mmol), 1,2-dibromobenzene (27.88 g, 118.19 mmol), sodium tert-butoxide (6.814 g, 70.908 mmol), palladium acetate (0.663 g, 2.95 mmol), and tri-tert-butylphosphine (1.19 g, 5.91 mmol) were dissolved in toluene (300 ml) and then oxygen was removed from the solution through nitrogen bubbling. After oxygen was removed, the mixture was refluxed and stirred for 24 hours. The reaction solution was extracted with methylene chloride, and then subjected to column chromatography using a methylene chloride/hexane mixed solvent as eluent to obtain 12.21 g of intermediate 22-1.

Intermediate 22-1:

Mass Spec (EI) m/z 324 [(M+H)$^+$]

[Scheme 2-2]

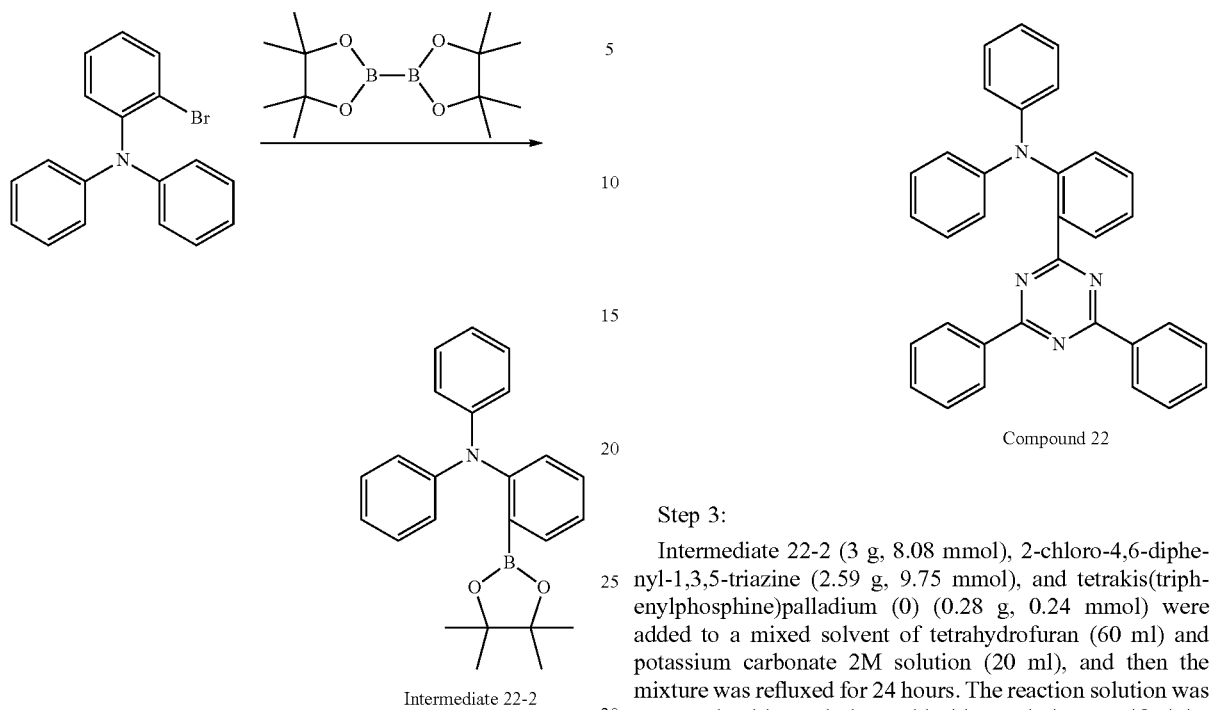

Compound 22

Step 2:

Intermediate 22-1 (10 g, 30.84 mmol), 4,4,4',4',5,5,5',5'-octamethyl-2,2'-bi(1,3,2-dioxaborane) (11.74 g, 46.26 mmol), potassium acetate (9.08 g, 92.52 mmol), and 1,1'-bis(diphenylphosphino)ferrocene-palladium(II) dichloride dichloromethane complex (0.76 g, 0.93 mmol) were dissolved in 1,4-dioxane (180 ml) and then oxygen was removed from the solution through nitrogen bubbling. After oxygen was removed, the mixture was refluxed and stirred for 24 hours. The reaction solution was extracted with methylene chloride, and then subjected to column chromatography using a methylene chloride/hexane mixed solvent as eluent to obtain 4.58 g of intermediate 22-2.

Intermediate 22-2:

Mass Spec (EI) m/z 371 [(M+H)$^+$].

Step 3:

Intermediate 22-2 (3 g, 8.08 mmol), 2-chloro-4,6-diphenyl-1,3,5-triazine (2.59 g, 9.75 mmol), and tetrakis(triphenylphosphine)palladium (0) (0.28 g, 0.24 mmol) were added to a mixed solvent of tetrahydrofuran (60 ml) and potassium carbonate 2M solution (20 ml), and then the mixture was refluxed for 24 hours. The reaction solution was extracted with methylene chloride, and then purified by column chromatography using a methylene chloride/hexane mixed solvent as eluent, and finally 3.08 g of compound 22 as a pure white solid was obtained through sublimation purification.

Compound 22:

yield 86% Mass Spec (EI) m/z 476 [(M+H)$^+$]. Elemental analysis theoretical value $C_{33}H_{24}N_4$: C, 83.17%; H, 5.08%; N, 11.76%. Measured: C, 82.16%; H, 5.12%; N, 11.77%. $^1$H NMR (500 MHz, CDCl$_3$): δ 8.83 (d, 1H), 8.51 (d, 4H), 8.05 (d, 1H), 7.64~7.61 (m, 2H), 7.57~7.53 (m, 3H), 7.46 (t, 4H), 7.41 (d, 2H), 7.09~7.04 (m, 5H), 6.83~6.79 (m, 2H).

Synthesis Example 6: Synthesis of Compound 23

[Scheme 2-3]

[Scheme 3]

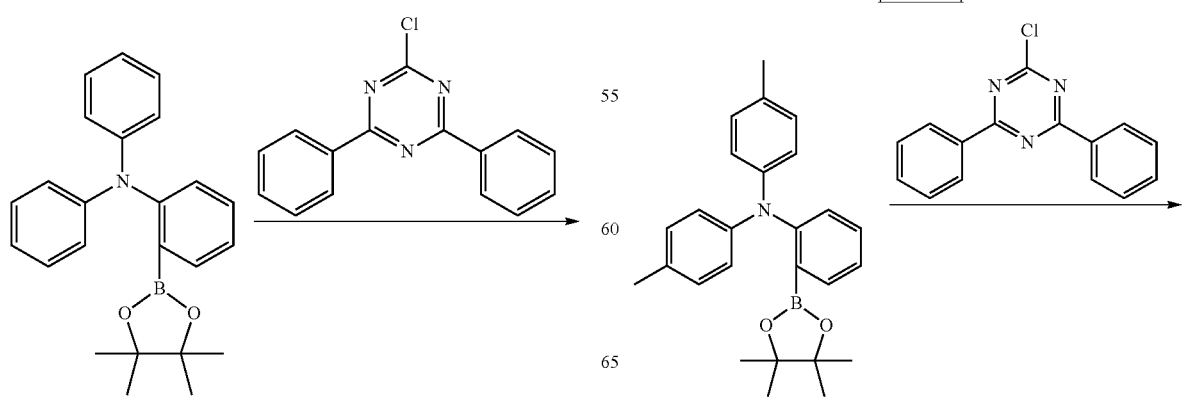

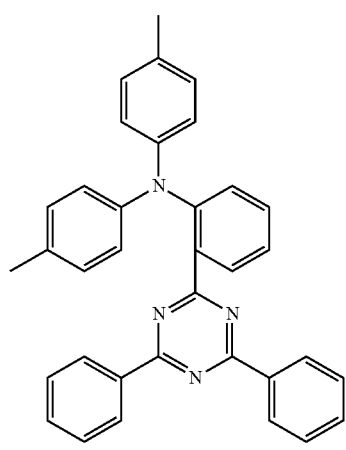

Compound 23

Compound 23 was obtained in a yield of 78% using the same method as in Synthesis Example 5 except that di-p-tolylamine was used instead of diphenylamine in Step 1 of Synthesis Example 5 to obtain 2-(4,4,5,5-tetramethyl-1,3,2-dioxaboran-2-yl)-N,N-di-p-tolylaniline in Step 2 and this was used in Step 3.

Compound 23:

Mass Spec (EI) m/z 504 [(M+H)$^+$]. Elemental analysis theoretical value $C_{35}H_{28}N_4$: C (83.30%) H (5.59%) N (11.10%) Measured: C, 83.32%; H, 5.66%; N, 11.05%. $^1$H NMR (500 MHz, CDCl$_3$): 8.52 (d, 4H), 7.95 (d, 1H), 7.56 (t, 2H), 7.53~7.45 (m, 5H), 7.38~7.32 (m, 2H), 6.92 (d, 4H), 6.85 (d, 4H).

Synthesis Example 7: Synthesis of Compound 36

[Scheme 4-1]

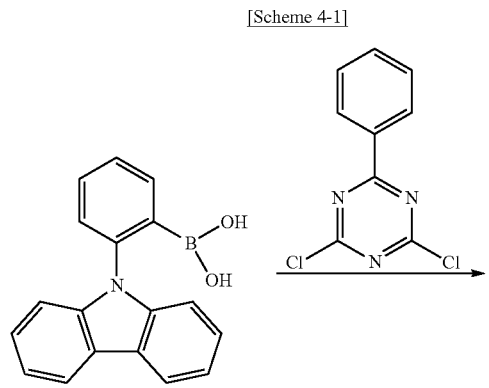

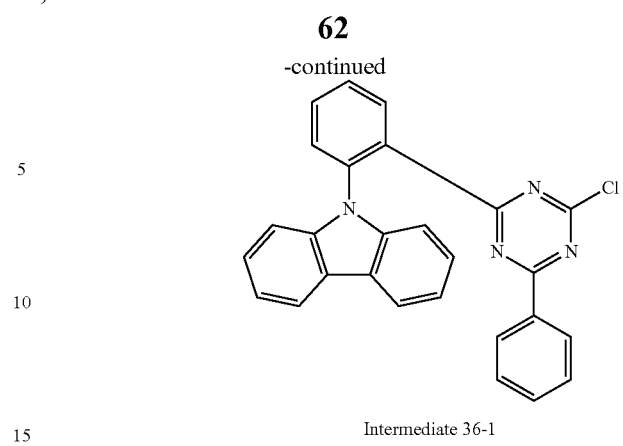

Intermediate 36-1

(2-(carbazol-9-yl)phenyl)boronic acid (10 g, 34.83 mmol), 2,4-dichloro-6-phenyl-1,3,5-triazine (7.87 g, 34.83 mmol), tetrakis(triphenylphosphine)palladium (0) (4.02 g, 3.48 mmol), and potassium carbonate (14.44 g, 104.49 mmol) were added to tetrahydrofuran (60 ml), distilled water (20 ml), and then the mixture was refluxed and stirred for 24 hours. The reaction solution was extracted with methylene chloride, and then subjected to column chromatography using a methylene chloride/hexane mixed solvent as eluent to obtain 7.99 g of intermediate 36-1.

Intermediate 36-1:

Mass Spec (EI) m/z 432 [(M+H)$^+$].

[Scheme 4-2]

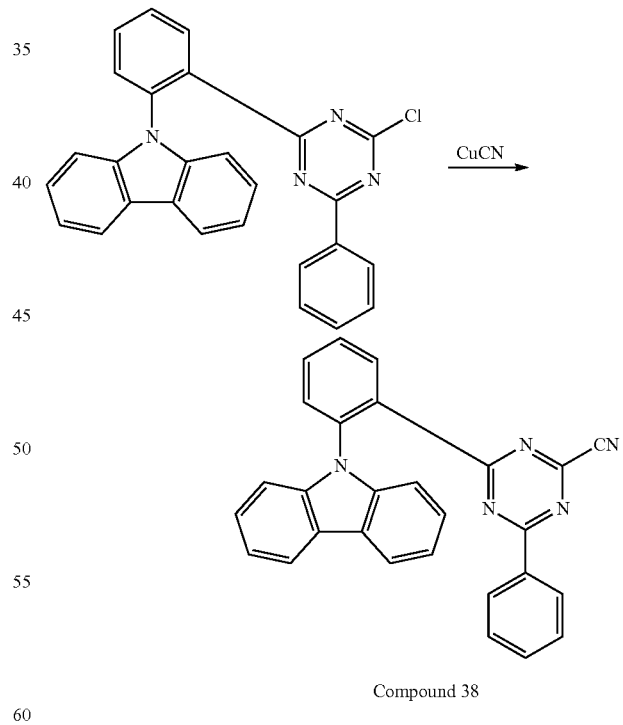

Compound 38

Intermediate 36-1 (3 g, 6.94 mmol) and copper cyanide (2.18 g, 24.31 mmol) were dissolved in N-methyl-2-pyrrolidone (50 ml) and then oxygen was removed from the solution through nitrogen bubbling. After oxygen was removed, the mixture was refluxed and stirred for 24 hours. The reaction solution was extracted with methylene chloride, and then subjected to column chromatography using a methylene chloride/hexane mixed solvent as eluent to obtain 2.49 g of Compound 36.

Compound 36:

Mass Spec (EI) m/z 423 [(M+H)⁺]. Elemental analysis theoretical value $C_{28}H_{17}N_5$: C (79.42%) H (4.05%) N (16.54%) Measured: C, 79.43%; H, 4.07%; N, 16.51%. $^1$H NMR (500 MHz, CDCl$_3$): 8.41 (d, 1H), 8.02 (d, 2H), 7.85 (t, 1H), 7.75~7.70 (m, 2H), 7.36~7.29 (m, 5H), 7.22 (t, 2H), 7.15 (d, 2H), 7.10 (t, 2H).

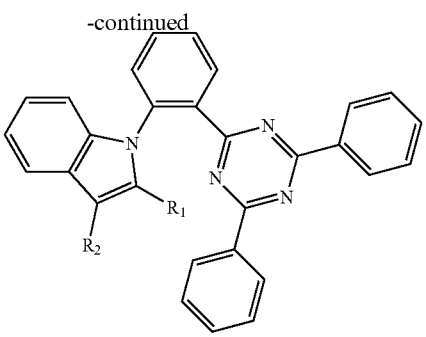

Compound 61 or 63

In Scheme 5, the product is Compound 61 when both of R$_1$ and R$_2$ are hydrogen, Compound 63 when R$_1$ is hydrogen and R$_2$ is a methyl group.

Synthesis Example 8: Synthesis of Compound 61

Step 1:
2-chloro-4,6-diphenyl-1,3,5-triazine (5.0 g, 18.67 mmol), (2-fluorophenyl) boronic acid (3.92 g, 28.01 mmol), tetrakis (triphenylphosphine) palladium (0) (2.15 g, 1.86 mmol), potassium carbonate (7.74 g, 56.03 mmol) were dissolved in toluene (120 ml), ethanol (60 ml), D.W (90 ml), and then oxygen was removed from the solution through nitrogen bubbling. After oxygen was removed, the mixture was stirred at room temperature for 1 hour and then refluxed and stirred at 130° C. for 15 hours. Then, the reaction solution was vacuum-dried by removing the solvent through a rotary evaporator. The dried mixture was extracted with methylene chloride and then subjected to column chromatography using a methylene chloride/hexane mixed solvent as eluent to obtain 5.4 g of 2-(2-fluorophenyl)-4,6-diphenyl-1,3,5-triazine.

2-(2-fluorophenyl)-4,6-diphenyl-1,3,5-triazine: Mass Spec (EI) m/z 327 [(M+H)⁺] $^1$H NMR (500 MHz, CDCl$_3$): 8.76 (d, 4H), 8.48 (t, 1H), 7.62 (t, 3H), 7.56 (t, 4H), 7.35 (t, 1H), 7.27 (t, 1H).

Step 2:
2-(2-fluorophenyl)-4,6-diphenyl-1,3,5-triazine (1.00 g, 3.05 mmol), indole (0.89 g, 7.63 mmol), and sodium tertiary butoxide (0.73 g, 7.63 mmol) were mixed in a solvent of dimethylformamide (100 ml) and refluxed at 160° C. for 24 hours. The reaction solution was extracted with methylene chloride, and then purified by column chromatography using a methylene chloride/hexane mixed solvent as eluent, and finally 0.63 g of Compound 61 as a yellow solid was obtained through sublimation purification.

Compound 61:
yield 49.5% Mass Spec (EI) m/z 424 [(M+H)⁺]. Elemental analysis theoretical value $C_{29}H_{20}N_4$: C (82.05%) H (4.75%) N (13.20%) Measured: C, 81.98%; H, 4.77%; N, 13.11%. $^1$H NMR (500 MHz, CDCl$_3$): 8.42 (d, 1H), 8.16 (d, 4H), 7.73 (t, 1H), 7.66 (t, 2H), 7.61 (d, 1H), 7.50 (t, 2H), 7.38 (t, 4H), 7.31 (d, 1H), 7.19~7.13 (m, 2H), 7.07 (d, 1H), 6.53 (d, 1H).

Synthesis Example 9: Synthesis of Compound 63

1.17 g of Compound 63 was obtained in a similar manner to that of Step 2 of Synthesis Example 8, except that 2-(2-fluorophenyl)-4,6-diphenyl-1,3,5-triazine (1.50 g, 4.58 mmol) obtained in Step 1 of Synthesis Example 8, 3-methylindole (1.50 g, 11.45 mmol), and sodium tertiary butoxide (1.10 g, 11.45 mmol) were added to a solvent of dimethylformamide (100 ml).

Compound 63:

yield 58.07% Mass Spec (EI) m/z 438 [(M+H)+]. Elemental analysis theoretical value $C_{30}H_{22}N_4$: C (82.17%) H (5.06%) N (12.78%), Measured: C, 82.22%; H, 4.97%; N, 12.69%. $^1$H NMR (500 MHz, CDCl$_3$): 8.43 (d, 1H), 8.20 (d, 4H), 7.71 (t, 1H), 7.62 (t, 2H), 7.52 (t, 3H), 7.39 (t, 4H), 7.19~7.17 (m, 1H), 7.10~6.94 (m, 2H), 6.94 (s, 1H), 2.26 (s, 3H).

Synthesis Example 10: Synthesis of Compound 52 with methylene chloride, and then purified by column chromatography using methylene chloride/hexane mixed solvent as eluent, and finally 1.35 g of a yellow solid Compound 52 was obtained through sublimation purification.

Compound 52:

yield 78.4%, Mass Spec (EI) m/z 565 [(M+H)+]. $^1$H NMR (300 MHz, DMSO): 7.16~7.26 (m, 6H), 7.34~7.51 (m, 6H), 7.82 (d, 1H), 7.88~7.99 (m, 6H), 8.03~8.31 (m, 3H), 8.30 (d, 1H), 8.60 (d, 1H).

Synthesis Example 11: Synthesis of Compound 67

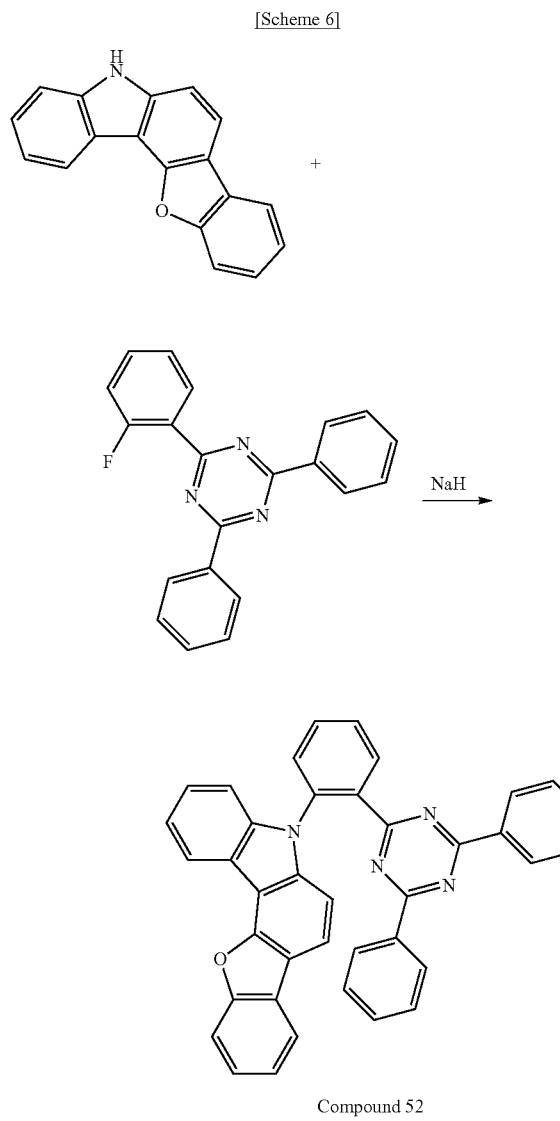

Compound 52

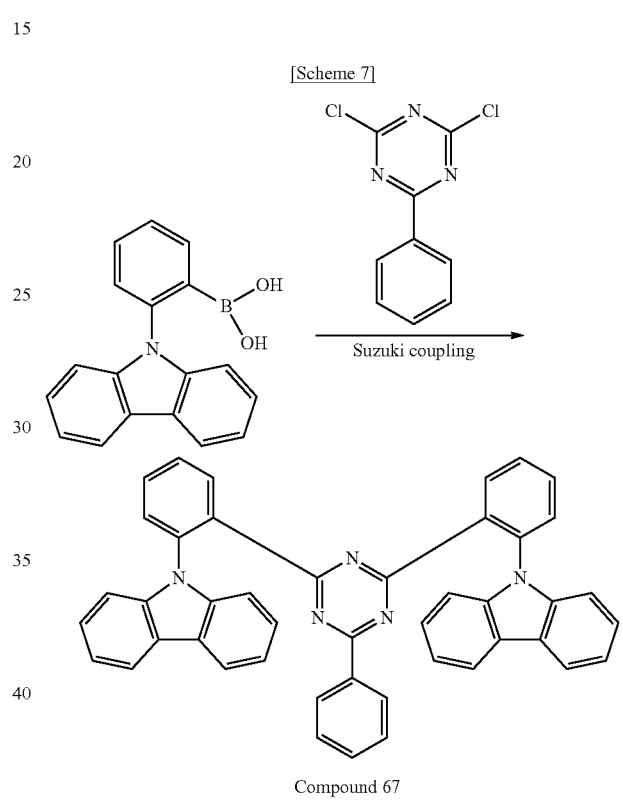

Compound 67

2-(2-fluorophenyl)-4,6-diphenyl-1,3,5-triazine (1.00 g, 3.05 mmol), 5H-benzofuro[3,2-c] carbazole (0.98 g, 3.82 mmol), sodium hydride (0.10 g, 3.90 mmol) were mixed in a solvent of dimethylformamide (100 ml) and refluxed at 160° C. for 24 hours. The reaction solution was extracted 9-(2-(4,4,5,5-tetramethyl-1,3,2-dioxaborolane-2-yl)phenyl)carbazole (8.0 g, 27.9 mmol), 2,4-dichloro-6-phenyl-1,3,5-triazine (3.0 g, 13.3 mmol), and tetrakis (triphenylphosphine) palladium (0) (1.53 g, 1.33 mmol) were added to a mixed solvent of tetrahydrofuran (100 ml) and potassium carbonate 2M solution (40 ml) and refluxed for 24 hours. The reaction solution was extracted with methylene chloride, and then purified by column chromatography using methylene chloride/hexane mixed solvent as eluent, and finally a pure white solid was obtained in a yield of 71% through sublimation purification.

Compound 67:

Mass Spec (EI) m/z 639 [(M+H)+]. Elemental analysis theoretical value $C_{45}H_{29}N_5$ C (84.48%) H (4.57%) N (10.95%) Measured: C (84.48%) H (4.57%) N (10.86%). $^1$H NMR (500 MHz, CDCl$_3$): δ 6.79 (d, 2H, J=8 Hz), 6.895 (t, 2H, J=15 Hz), 6.965 (d, 4H, J=8 Hz), 7.163~7.217 (m, 5H), 7.263 (t, 4H, J=15 Hz), 7.478 (t, 2H, J=15 Hz), 7.563 (d, 2H, J=8 Hz), 7.659~7.708 (m, 4H), 7.986 (d, 4H, J=8 Hz).

Synthesis Example 12: Synthesis of Compound 83

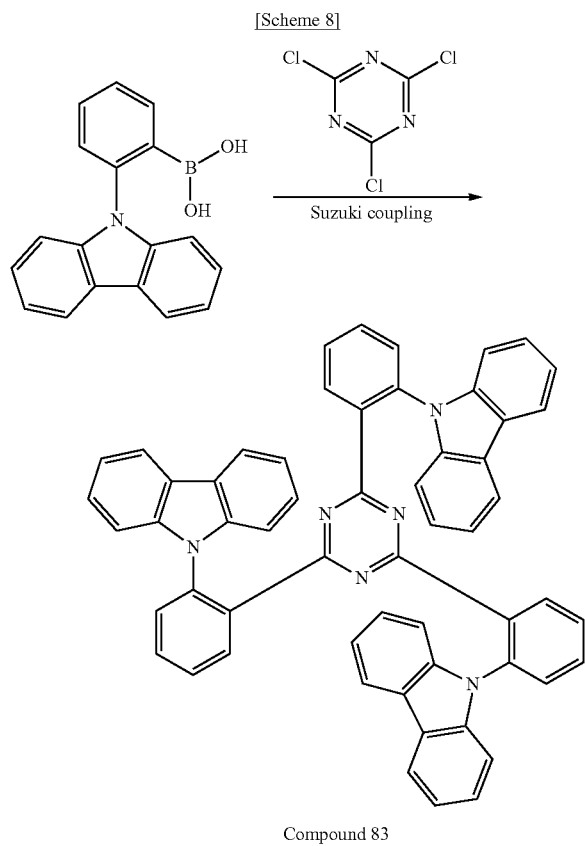

Compound 83

9-(2-(4,4,5,5-tetramethyl-1,3,2-dioxaborolane-2-yl)phenyl)carbazole (15.4 g, 53.7 mmol), cyanuric chloride (3.0 g, 16.3 mmol), and tetrakis(triphenylphosphine)palladium (0) (2.82 g, 2.44 mmol) were added to a mixed solvent of tetrahydrofuran (100 ml) and potassium carbonate 2M solution (40 ml) and refluxed for 24 hours. The reaction solution was extracted with methylene chloride, and then purified by column chromatography using methylene chloride/hexane mixed solvent as eluent, and finally a pure white solid was obtained in a yield of 37% through sublimation purification.

Compound 83:

Mass Spec (EI) m/z 803 [(M+H)$^+$]. Elemental analysis theoretical value $C_{57}H_{36}N_6$ C (85.05%) H (4.51%) N (10.44%) Measured: C (85.07%) H (4.49%) N (10.45%). $^1$H NMR (500 MHz, CDCl$_3$): δ 6.238 (d, 3H, J=8 Hz), 6.558 (d, 6H, J=8 Hz), 6.968 (t, 3H, J=15 Hz), 7.216~7.261 (m, 12H), 7.341 (d, 3H, J=8 Hz), 7.485 (t, 3H, J=15 Hz), 8.10 (d, 6H, J=7 Hz)

Preparation Example 1: Preparation of Delayed Fluorescent Organic Light Emitting Diode (ITO/PEDOT:PSS/TAPC/mCP/mCP:Compound 1/TSPO1/TPBi/LiF/Al)

A glass substrate on which an anode, ITO, was deposited was ultrasonically cleaned for 30 minutes using pure water and isopropyl alcohol. The cleaned ITO substrate was surface-treated using ultraviolet rays of short wavelength, and then a hole injection layer was formed by spin coating PEDOT: PSS (poly (3,4-ethylenedioxythiophene): poly (styrenesulfonate)) to a thickness of 60 nm. Thereafter, TAPC (1,1-Bis[4-[N,N'-Di(p-tolyl)Amino]Phenyl]Cyclohexane was vapor-deposited at a pressure of 1×10$^{-6}$ torr at a rate of 0.1 nm/s to form a hole transporting layer of 20 nm. Thereafter, mCP (N, N-dicarbazolyl-3,5-benzene) was vapor-deposited at a pressure of 1×10$^{-6}$ torr at a rate of 0.1 nm/s to form a exciton blocking layer of 10 nm. Subsequently, under a pressure of 1×10$^{-6}$ torr, mCP as a host material at a rate of 0.1 nm/s and Compound 1 as a delayed fluorescent dopant material synthesized through Synthesis Example 1 at a rate of 0.005 nm/s were co-evaporated to form a light emitting layer doped with 5% of the dopant in the host. TSPO1 (diphenylphosphine oxide-4-(triphenylsilyl)phenyl) and TPBi (1,3,5-tris (N-phenylbenzimidazol-2-yl) benzene) were sequentially vapor-deposited at a pressure of 1×10$^{-6}$ torr at a rate of 0.1 nm/s to form an exciton blocking layer of 5 nm and an electron transport layer of 30 nm, respectively. Thereafter, LiF as an electron injecting material was vapor-deposited at a pressure of 1×10$^{-6}$ torr at a rate of 0.01 nm/s to form an electron injecting layer of 1 nm. Thereafter, Al was vapor-deposited at a rate of 0.5 nm/sec under a pressure of 1×10$^{-6}$ torr to form a cathode of 100 nm, thereby forming an organic light-emitting diode. After formation of the device, the device was sealed using a CaO moisture absorbent and a glass cover glass.

The organic light emitting device using Compound 1 as a fluorescent dopant material has a quantum efficiency of 9.3%, a current efficiency of 14.6 cd/A, a power efficiency of 7.6 lm/W at a voltage of 6 V, x=0.15 and y=0.22 based on CIE 1931 color coordinates, indicating excellent blue light emission characteristics. These results exceeded the limit of the maximum external quantum efficiency of 5% (20% of the light extraction efficiency) that can be obtained from a general fluorescent device, and it can be a direct proof that a triplet energy is converted into a single energy by inter-system crossing, which is the property of the thermally-activated delayed fluorescent material.

Preparation Example 2: Preparation of Delayed Fluorescent Organic Light Emitting Diode (ITO/PEDOT:PSS/TAPC/mCP/mCP: Compound 2/TSPO1/TPBi/LiF/Al)

An organic light emitting diode was fabricated in the same manner as in Preparation Example 1, except that Compound 2 synthesized through Synthesis Example 2 was used as a delayed fluorescent dopant material.

The organic light emitting diode according to Preparation Example 2 using Compound 2 as a light emitting dopant material showed, at a voltage of 6 V, a quantum efficiency of 14.7%, a current efficiency of 30.9 cd/A, a power efficiency of 14.9 lm/W and x=0.17 and y=0.34 based on a CIE 1931 color coordinate, indicating excellent blue light emission characteristics.

Preparation Example 3: Preparation of Delayed Fluorescent Organic Light Emitting Diode (ITO/PEDOT:PSS/TAPC/mCP/mCP:Compound 3/TSPO1/TPBi/LiF/Al)

An organic light emitting diode was fabricated in the same manner as in Preparation Example 1, except that Compound 3 synthesized through Synthesis Example 3 was used as a delayed fluorescent dopant material.

The organic light emitting diode according to Preparation Example 3 using Compound 3 as a light emitting dopant material showed, at a voltage of 6 V, a quantum efficiency of 12.3%, a current efficiency of 24.0 cd/A, a power efficiency of 12.6 lm/W and x=0.16 and y=0.30 based on a CIE 1931 color coordinate, indicating excellent blue light emission characteristics.

Preparation Example 4: Preparation of Delayed Fluorescent Organic Light Emitting Diode (ITO/PEDOT:PSS/TAPC/mCP/mCP:Compound 37/TSPO1/TPBi/LiF/Al)

An organic light emitting diode was fabricated in the same manner as in Preparation Example 1, except that Compound 37 synthesized through Synthesis Example 4 was used as a delayed fluorescent dopant material.

The organic light emitting diode according to Preparation Example 4 using Compound 37 as a light emitting dopant material showed, at a voltage of 6 V, a quantum efficiency of 11.5%, a current efficiency of 29.1 cd/A, a power efficiency of 13.8 lm/W and x=0.16 and y=0.20 based on a CIE 1931 color coordinate, indicating excellent blue light emission characteristics.

Preparation Example 5: Preparation of Delayed Fluorescent Organic Light Emitting Diode (ITO/PEDOT:PSS/TAPC/mCP/mCP:Compound 22/TSPO1/TPBi/LiF/Al)

An organic light emitting diode was fabricated in the same manner as in Preparation Example 1, except that Compound 22 synthesized through Synthesis Example 5 was used as a delayed fluorescent dopant material.

The organic light emitting diode according to Preparation Example 5 using Compound 22 as a light emitting dopant material showed, at a voltage of 9 V, a quantum efficiency of 17.2%, a current efficiency of 45.0 cd/A, a power efficiency of 31.4 lm/W and x=0.21 and y=0.45 based on a CIE 1931 color coordinate, indicating excellent blue-green light emission characteristics.

Preparation Example 6: Preparation of Delayed Fluorescent Organic Light Emitting Diode (ITO/PEDOT:PSS/TAPC/mCP/mCP: Compound 52/TSPO1/TPBi/LiF/Al)

An organic light emitting diode was fabricated in the same manner as in Preparation Example 1, except that Compound 52 synthesized through Synthesis Example 10 was used as a delayed fluorescent dopant material.

The organic light emitting diode according to Preparation Example 6 using Compound 52 as a light emitting dopant material showed, at a voltage of 9 V, a quantum efficiency of 12.5%, a current efficiency of 19.8 cd/A, a power efficiency of 17.8 lm/W and x=0.15 and y=0.20 based on a CIE 1931 color coordinate, indicating excellent blue light emission characteristics.

Preparation Example 7: Preparation of Delayed Fluorescent Organic Light Emitting Diode (ITO/PEDOT:PSS/TAPC/mCP/mCP:Compound 23/TSPO1/TPBi/LiF/Al)

An organic light emitting diode was fabricated in the same manner as in Preparation Example 1, except that Compound 23 synthesized through Synthesis Example 6 was used as a delayed fluorescent dopant material.

The organic light emitting diode according to Preparation Example 7 using Compound 23 as a light emitting dopant material showed, at a voltage of 9 V, a quantum efficiency of 16.3%, a current efficiency of 54.6 cd/A, a power efficiency of 32.8 lm/W and x=0.35 and y=0.58 based on a CIE 1931 color coordinate, indicating excellent green light emission characteristics.

Preparation Example 8: Preparation of Delayed Fluorescent Organic Light Emitting Diode (ITO/PEDOT:PSS/TAPC/mCP/mCP:Compound 36/TSPO1/TPBi/LiF/Al)

An organic light emitting diode was fabricated in the same manner as in Preparation Example 1, except that Compound 36 synthesized through Synthesis Example 7 was used as a delayed fluorescent dopant material.

The organic light emitting diode according to Preparation Example 8 using Compound 36 as a light emitting dopant material showed, at a voltage of 6 V, a quantum efficiency of 11.7%, a current efficiency of 26.9 cd/A, a power efficiency of 10.4 lm/W and x=0.55 and y=0.45 based on a CIE 1931 color coordinate, indicating excellent orange light emission characteristics.

Preparation Example 9: Preparation of Delayed Fluorescent Organic Light Emitting Diode (ITO/PEDOT:PSS/TAPC/mCP/mCP:Compound 67/TSPO1/TPBi/LiF/Al)

An organic light emitting diode was fabricated in the same manner as in Preparation Example 1, except that Compound 67 synthesized through Synthesis Example 11 was used as a delayed fluorescent dopant material.

The organic light emitting diode according to Preparation Example 9 using Compound 67 as a light emitting dopant material showed, at a voltage of 8 V, a quantum efficiency of 12.2%, a current efficiency of 18.5 cd/A, a power efficiency of 6.47 lm/W and x=0.17 and y=0.21 based on a CIE 1931 color coordinate, indicating excellent blue light emission characteristics.

Preparation Example 10: Preparation of Delayed Fluorescent Organic Light Emitting Diode (ITO/PEDOT:PSS/TAPC/mCP/mCP:Compound 83/TSPO1/TPBi/LiF/Al)

An organic light emitting diode was fabricated in the same manner as in Preparation Example 1, except that Compound 83 synthesized through Synthesis Example 12 was used as a delayed fluorescent dopant material.

The organic light emitting diode according to Preparation Example 9 using Compound 83 as a light emitting dopant material showed, at a voltage of 8 V, a quantum efficiency of 14.9%, a current efficiency of 23.0 cd/A, a power efficiency of 9.57 lm/W and x=0.15 and y=0.22 based on a CIE 1931 color coordinate, indicating excellent blue light emission characteristics.

Comparative Example 1: Preparation of Delayed Fluorescent Organic Light Emitting Diode (ITO/PEDOT:PSS/TAPC/mCP/mCP:CC2TA/TSPO1/TPBi)LiF/Al)

An organic light emitting diode was fabricated in the same manner as in Preparation Example 1, except that 2,4-bis 3-(9H-carbazol-9-yl)-9H-carbazol-9-yl-6-phenyl-1,3,5-triazine (CC2TA) reported in the paper (APPLIED PHYSICS LETTERS 101, 093306 (2012)) was used as a delayed fluorescent dopant material.

The organic light emitting diode according to Comparative Example 1 using CC2TA as a light emitting dopant material showed, at a voltage of 6 V, a quantum efficiency of 11.5%, a current efficiency of 29.1 cd/A, a power efficiency of 13.8 lm/W and x=0.20 and y=0.44 based on a CIE 1931 color coordinate.

Blue (Preparation Examples 1-4, 6, 9 and 10), green (Preparation Examples 5 and 7) and red (Preparation Example 8) organic light emitting diodes were prepared by using the thermally activated delayed fluorescent compounds in the Preparation Examples 1-10. Each of these organic light emitting diodes exhibits a quantum efficiency exceeding 5% (a light extraction efficiency is 20%) which is the maximum external quantum efficiency that can be obtained from a general fluorescent device, indicating that the thermally activated delayed fluorescence compounds according to examples of the present invention facilitates efficient reverse intersystem crossing from triplet state to singlet state. In addition, the organic light emitting diode according to Comparative Example 1 using CC2TA, which is known as a conventional delayed fluorescent light emitting material, exhibits a quantum efficiency of 11.5%, whereas the organic light emitting diodes according to Examples 2 to 10 exhibit significantly higher or the same quantum efficiency. In particular, the green light emitting device (Preparation Example 5) exhibits a high quantum efficiency of 17% or more, showing excellent luminescence characteristics as compared with the conventional fluorescent device.

Table 1 below shows the values calculated by the molecular calculation technique for Compound 1 prepared according to Synthesis Example 1, Comparative Compound A, and Comparative Compound B. Molecular calculations were performed using the Gaussian 09 program through the B3LYP method according to density functional theory on a 6-31 G * basis set.

TABLE 1

| Sample | Structural Formula | 1)$B_g$ | 2)$S_1$ | 3)$T_1$ | 4)$\Delta E_{ST}$ | 5)HOMO | 6)LUMO |
| --- | --- | --- | --- | --- | --- | --- | --- |
| Compound (ortho) | (1) | 3.49 eV | 2.86 eV | 2.79 eV | 0.06 eV | −5.31 eV | −1.81 eV |
| Comparative Compound A (meta) | | 3.39 eV | 2.90 eV | 2.75 eV | 0.15 eV | −5.36 eV | −1.97 eV |
| Comparative Compound B (para) | | 3.47 eV | 3.04 eV | 2.70 eV | 0.34 eV | −5.42 eV | −1.95 eV |

1)Bandgap,
2)Singlet Energy,
3)Triplet Energy,
4)Difference between the singlet energy and the triplet energy,
5)Highest occupied molecular orbital Energy level,
6)Lowest unoccupied molecular orbital Energy level Referring to Table 1, Comparative Compound A or B is in a form similar to Compound 1, but carbazole as an electron donating group and diphenyltriazine as an electron withdrawing group are in meta position in Comparative Compound A and in para position in Comparative Compound B. Calculation result shows that, as the position of the carbazole and diphenyltriazine were shifted from ortho to meta, and from metal to para, the singlet energy gradually increased and the triplet energy gradually decreased. As a result, the smallest energy different was found between the singlet state and the triplet state in the ortho form. The smaller energy difference between the singlet state and the triplet state is, the easier the Reverse Intersystem Crossing (RISC) is, and the better the thermally activated delay fluorescence property can be obtained.

Figure 2:
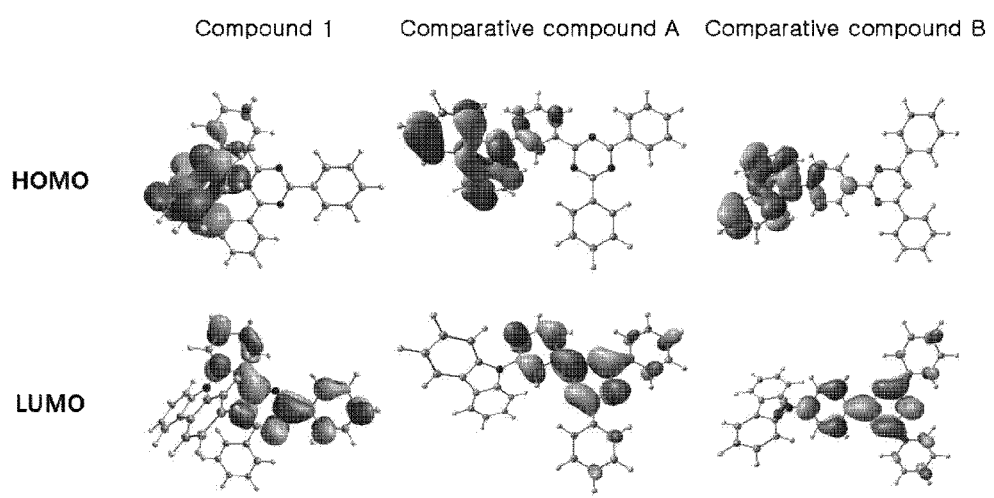
FIG. 2 shows distribution of molecular orbital of Compound 1 prepared according to Synthesis Example 1, Comparative Compound 2, and Comparative Compound 3.

FIG. 2 shows the molecular orbital distribution of Compound 1 prepared according to Synthesis Example 1, Comparative Compound A and Comparative Compound B. The molecular orbital distribution was calculated using the Gaussian 09 program through the B3LYP method according to density functional theory with a 6-31 G * basis set.

In order to show the fluorescence property effectively, the overlapping between HOMO and LUMO should exist at a certain level. As a result of calculation, HOMO and LUMO of ortho, meta and para forms are overlapped on benzene which is the central connecting unit, the fluorescence property of the ortho-form material was expected to be similar to other-form materials. These results indicate that the ortho-form material can up-convert the triplet exciton formed during electroluminescence to the singlet exciton more effectively through RISC than the meta- and para-form materials, and the singlet exciton can show effective fluorescent light emitting.

The present invention is not limited to the above-described embodiments and the accompanying drawings. While the example embodiments of the present invention and their advantages have been described in detail, it should be understood that various changes, substitutions, and alterations may be made herein without departing from the scope of the present invention.

The invention claimed is:

1. The light-emitting material represented by Chemical Formula 3:

[Chemical Formula 3]

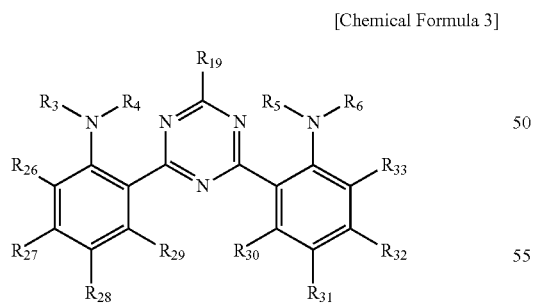

wherein in Chemical Formulas 3;

$R_3$ and $R_4$ are combined together with the nitrogen to which they are attached to independently form a substituted or unsubstituted heteroaryl group represented by any one of Structural Formulas A9 or A24, and $R_5$ and $R_6$ are combined together with the nitrogen to which they are attached to independently form a substituted or unsubstituted heteroaryl group represented by any one of Structural Formulas A9 or A24:

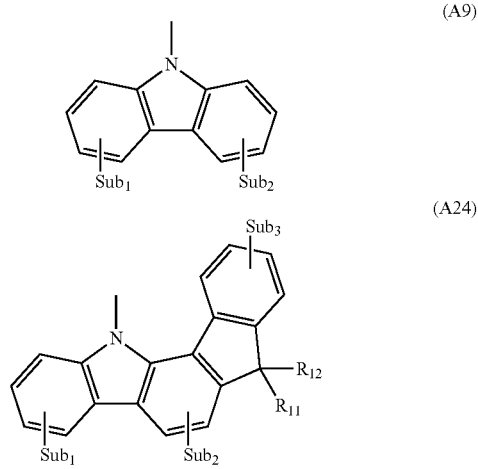

wherein in Structural Formulas A9 and A24:

$R_{11}$ and $R_{12}$ are, each independently, hydrogen, deuterium, a substituted or unsubstituted C1-C2 alkyl group, or a substituted or unsubstituted C6-C30 aryl group in Formula A9, $Sub_1$ and $Sub_2$ are, each independently, deuterium, a substituted or unsubstituted C5-C30 cycloalkyl group, a substituted or unsubstituted C6-C30 aryl group, a substituted or unsubstituted C6-C30 alkylaryl group, a substituted or unsubstituted C6-C30 aralkyl group, a substituted or unsubstituted C3-C30 heteroaryl group, a substituted or unsubstituted C1-C9 alkyloxy group, or a substituted or unsubstituted C6-C30 aryloxy group, in Formula A24, $Sub_1$ to $Sub_3$ are, each independently, hydrogen, deuterium, a substituted or unsubstituted C1-C9 alkyl group, a substituted or unsubstituted C5-C30 cycloalkyl group, a substituted or unsubstituted C6-C30 aryl group, a substituted or unsubstituted C6-C30 alkylaryl group, a substituted or unsubstituted C6-C30 aralkyl group, a substituted or unsubstituted C3-C30 heteroaryl group, a substituted or unsubstituted C1-C9 alkyloxy group, or a substituted or unsubstituted C6-C30 aryloxy group, $R_{19}$ is a substituted or unsubstituted C6 aryl group, and $R_{26}$ to $R_{33}$ are, each independently, hydrogen, deuterium, a halogen group, a substituted or unsubstituted C4-C6 aryl group, or a substituted or unsubstituted C1-C3 alkyl group.

2. The light-emitting material of claim 1, wherein the compound represented by Chemical Formula 3 is represented by the following Chemical Formula 6:

[Chemical Formula 6]

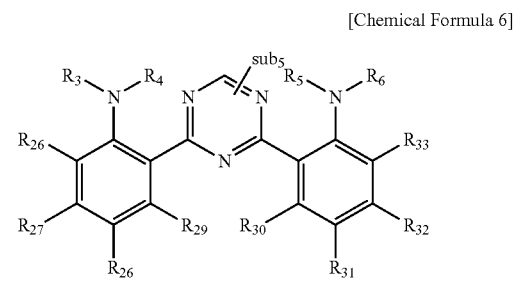

in Chemical Formula 6, $R_3$, $R_4$, $R_5$, $R_6$, $R_{26}$ to $R_{29}$, and $R_{30}$ to $R_{33}$ are as defined in Chemical Formula 3, Sub$_5$ is hydrogen, deuterium, a halogen group, a cyano group, a substituted or unsubstituted C1-C9 alkyl group, a substituted or unsubstituted C6-C30 aryl group, a substituted or unsubstituted C3-C30 heteroaryl group, a substituted or unsubstituted C1-C9 alkyloxy group, a substituted or unsubstituted —NR$_e$R$_f$, a substituted or unsubstituted silyl group, a substituted or unsubstituted phosphine group, a substituted or unsubstituted phosphine oxide group, a substituted or unsubstituted thiol group, a substituted or unsubstituted sulfoxide group, a substituted or unsubstituted sulfone group, a substituted or unsubstituted C5-C30 arylthio group, a substituted or unsubstituted C5-C30 aryloxy group, a substituted or unsubstituted C5-C30 arylamine group, or a substituted or unsubstituted C5-C30 aralkyl group; Sub$_5$ is optionally fused to a main body to which it is bonded to form a substituted or unsubstituted cyclyl or a substituted or unsubstituted aryl, R$_e$ and R$_f$ are independently selected from the group consisting of a substituted or unsubstituted C1-C9 alkyl group, a substituted or unsubstituted C5-C30 cycloalkyl group, a substituted or unsubstituted C6-C30 aryl group, a substituted or unsubstituted C6-C30 alkylaryl group, a substituted or unsubstituted C6-C30 aralkyl group, and a substituted or unsubstituted C3-C30 heteroaryl group; R$_e$ and R$_f$ are optionally joined together with the nitrogen to which they are attached to form a substituted or unsubstituted heterocyclyl or a substituted or unsubstituted heteroaryl.

3. A light-emitting material represented by any one of the following Compounds 68, 69, 71, 72, and 74:

(68)

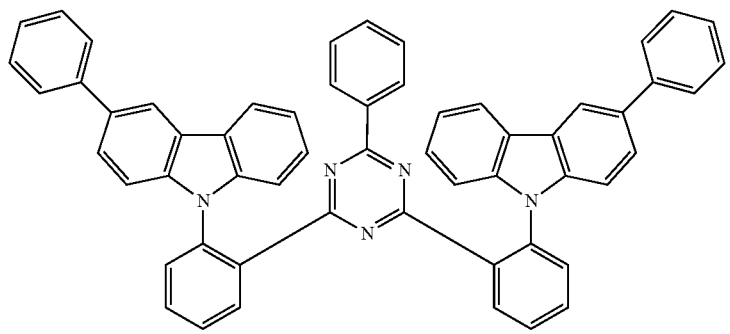

(69)

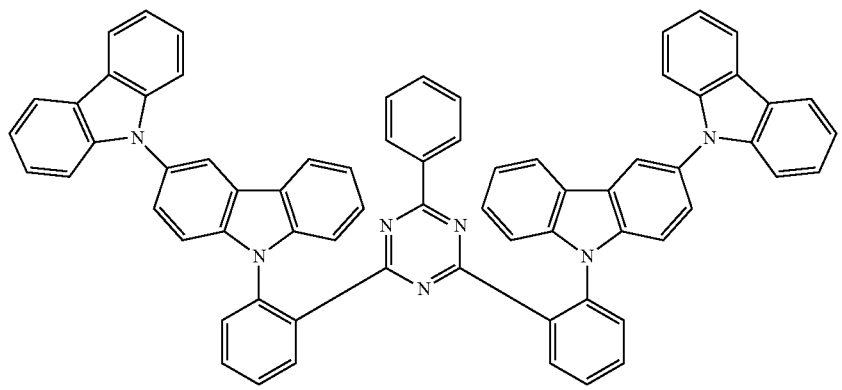

(71)

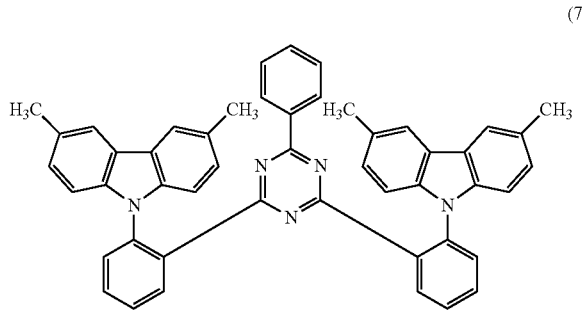

(72)

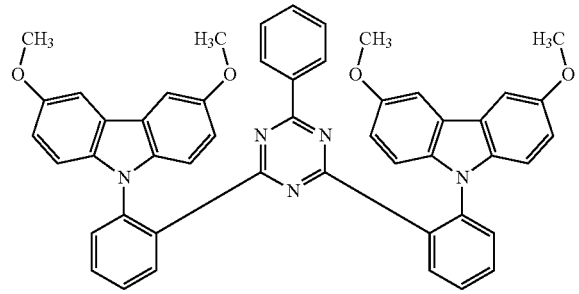

(74)
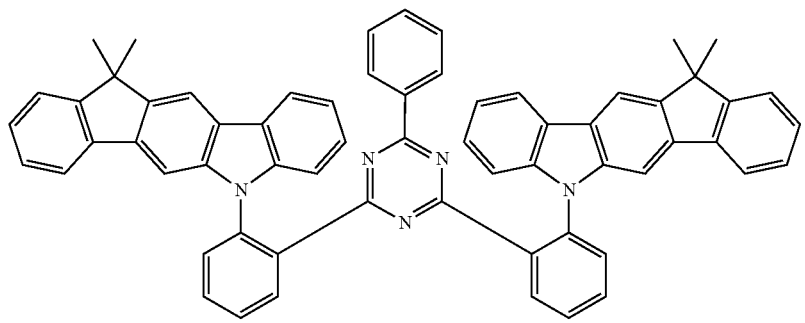
4. The light-emitting material of claim 1, wherein the triazine group in Chemical Formula 3 is any one of the following Structural Formulas B34 to B40:
(B34)
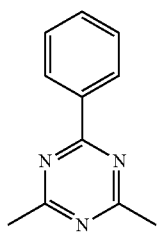
(B35)
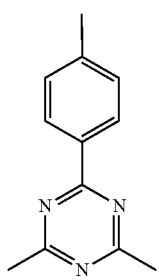
(B36)
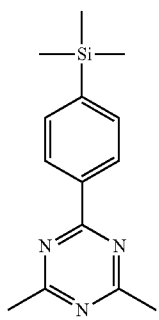
(B37)
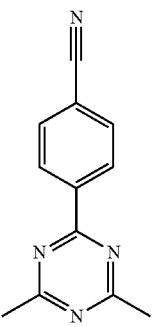
(B38)
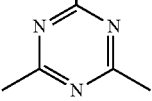
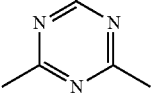
(B39)
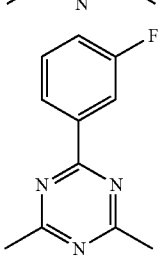
(B40)
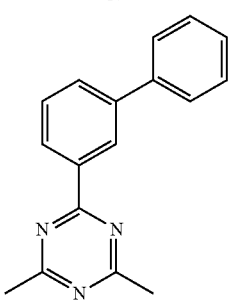
in Structural Formulas B34 to B40,
$R_{11}$ represents hydrogen, deuterium, or a substituted or unsubstituted C1-C2 alkyl group.

5. An organic light emitting diode comprising sequentially stacked an anode, a hole conduction layer, a light emitting layer, an electron conduction layer, and a cathode,
- wherein the hole conduction layer comprises a hole transporting layer;
- wherein the electron conduction layer comprises an electron transporting layer;
- wherein one of the hole transporting layer, the light emitting layer and the electron transporting layer comprises the light-emitting material of claim 1.

6. The organic light emitting diode of claim 5,
- wherein the light emitting layer comprises a host material and a dopant material, and the dopant material comprises the light-emitting material.

7. The organic light emitting diode of claim 6, wherein the dopant material is a delayed fluorescent light emitting material.

8. The light-emitting material of claim 1, wherein in Formula A24, $Sub_1$ to $Sub_3$ are each hydrogen.

9. The light-emitting material of claim 2, wherein $Sub_5$ is hydrogen.

10. The light-emitting material of claim 2, wherein $-NR_3R_4$ and $-NR_5R_6$ are each independently A9.

* * * * *